(12) United States Patent     (10) Patent No.:    US 8,721,684 B2
Denham et al.                               (45) Date of Patent:   *May 13, 2014

(54) METHOD AND APPARATUS FOR COUPLING ANATOMICAL FEATURES

(75) Inventors: Gregory J. Denham, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/412,127

(22) Filed: Mar. 5, 2012

(65) Prior Publication Data

US 2012/0165867 A1    Jun. 28, 2012

Related U.S. Application Data

(60) Division of application No. 12/196,407, filed on Aug. 22, 2008, now Pat. No. 8,137,382, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, which is a continuation-in-part of application No. 11/869,440, filed on Oct. 9, 2007, now Pat. No. 7,857,830, which is a continuation-in-part of application No. 11/784,821, filed on Apr. 10, 2007, which is a continuation-in-part of application No. 11/541,506, filed on Sep. 29, 2006, now Pat. No. 7,601,165, and a continuation-in-part of application No. 11/347,661, filed on Feb. 3, 2006, now Pat. No. 7,749,250, and a continuation-in-part of application No. 11/347,662, filed on Feb. 3, 2006, now abandoned.

(51) Int. Cl.
     *A61B 17/04*          (2006.01)

(52) U.S. Cl.
     USPC ........................ 606/232; 606/228; 623/13.14

(58) Field of Classification Search
     USPC ................. 606/139, 142, 144, 148, 228, 232; 623/13.14
See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

Invitation to Pay Additional Fees mailed Jul. 19, 2012, for PCT/US2012/037703 claiming benefit of U.S. Appl. No. 13/109,667, filed May 7, 2011.

(Continued)

*Primary Examiner* — Corrine M McDermott
*Assistant Examiner* — Alexander Orkin
(74) *Attorney, Agent, or Firm* — Harness, Dickey

(57) ABSTRACT

An assembly for coupling a first portion of an anatomy to a second portion of the anatomy includes an anchor having an anchor body and a first and second bores through the anchor body. A first adjustable suture construct having a body portion passes through the first bore of the anchor and includes first and second adjustable loops slidable relative to a passage portion defined in the body portion of the first adjustable suture construct. A similar second adjustable suture construct passes through the second bore of the anchor.

20 Claims, 21 Drawing Sheets

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevens |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et at |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |

(56) References Cited

U.S. PATENT DOCUMENTS

| | | |
|---|---|---|
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman et al. |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |

(56) References Cited

U.S. PATENT DOCUMENTS

| | | |
|---|---|---|
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |

(56) References Cited

U.S. PATENT DOCUMENTS

| | | |
|---|---|---|
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |

(56) References Cited

U.S. PATENT DOCUMENTS

| | | |
|---|---|---|
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |

(56) References Cited

U.S. PATENT DOCUMENTS

| | | |
|---|---|---|
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |

(56) References Cited

U.S. PATENT DOCUMENTS

| | | |
|---|---|---|
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |

(56) References Cited

U.S. PATENT DOCUMENTS

| | | |
|---|---|---|
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |

(56) References Cited

U.S. PATENT DOCUMENTS

| | | |
|---|---|---|
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,632,566 B2 | 1/2014 | Olson |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |

(56) References Cited

U.S. PATENT DOCUMENTS

| | | |
|---|---|---|
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |

(56) References Cited

U.S. PATENT DOCUMENTS

| | | |
|---|---|---|
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0026141 A1 | 2/2011 | Barrows |
| 2011/0046733 A1 | 2/2011 | Eggli |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0116409 A1 | 5/2012 | Stone |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0245585 A1 | 9/2012 | Kaiser et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0245761 A1 | 9/2013 | Conner et al. |

(56) References Cited

U.S. PATENT DOCUMENTS

| | | |
|---|---|---|
| 2013/0274812 A1 | 10/2013 | Dell'Oca |
| 2013/0289564 A1 | 10/2013 | Bernstein et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 440991 A1 | 8/1991 |
| EP | 0441065 | 8/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |

(56) References Cited

FOREIGN PATENT DOCUMENTS

| WO | WO-2012134999 A1 | 10/2012 |
|---|---|---|
| WO | WO-2012158583 A1 | 11/2012 |
| WO | WO-2013066974 A1 | 5/2013 |
| WO | WO-2013074525 A1 | 5/2013 |

OTHER PUBLICATIONS

"AperFix® System Surgical Technique Guide. Single Tunnel Double Bundle.™" Cayenne Medical brochure. (Aug. 2008) 8 sheets.
"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"Juggerknot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Interview Summary mailed Jul. 14, 2011 for U.S. Appl. No. 12/196,407.
Interview Summary mailed Jul. 14, 2011 for U.S. Appl. No. 12/196,410.
Interview Summary mailed Jul. 14, 2011 for U.S. Appl. No. 12/196,410, filed Aug. 22, 2008.
Interview Summary mailed Jun. 20, 2011 for U.S. Appl. No. 12/196,405.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Notice of Allowance (Supplemental Notice of Allowability) mailed Apr. 15, 2011 for U.S. Appl. No. 12/196,39, filed Aug. 22, 2008; now U.S. Patent No. 7,959,650.
Notice of Allowance (Supplemental Notice of Allowability) mailed Mar. 9, 2011 for U.S. Appl. No. 12/196,398, filed Aug. 22, 2008; now U.S. Patent No. 7,959,650.
Notice of Allowance mailed Oct. 13, 2011 for U.S. Appl. No. 12/196,410.
Notice of Allowance mailed Oct. 26, 2011 for U.S. Appl. No. 12/196,405.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Notice of Allowance mailed Jun. 1, 2009 for U.S. Appl. No. 11/541,506, filed Sep. 29, 2006; now U.S. Patent No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Patent No. 7,959,650.
Office Action mailed Dec. 7, 2011 for U.S. Appl. No. 12/589,168.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Patent No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Patent No. 7,658,751.
Restriction Requirement mailed Mar. 9, 2009 for U.S. Appl. No. 11/541,506, filed Sep. 29, 2006; now U.S. Patent No. 7,601,165.
Restriction Requirement mailed Sep. 29, 2010 for U.S. Appl. No. 12/196,398, filed Aug. 22, 2008; now U.S. Patent No. 7,959,650.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, a Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.

(56) References Cited

OTHER PUBLICATIONS

Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
"Suture Tensioner w/Tensiometer," Arthrex®, Inc. catalog "Next Generation in Knee Ligament Reconstruction & Repair Technology," 2009.
"TriTis™ Tibial Fixation System and Implant" brochure. Scandius Biomedical (2006).
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.
Office Action mailed Oct. 24, 2012 for U.S. Appl. No. 13/399,125.
Office Action mailed Sep. 21, 2012 for U.S. Appl. No. 13/098,897.
Office Action mailed Sep. 24, 2012 for U.S. Appl. No. 13/098,927.
Office Action mailed Feb. 10, 2012 for U.S. Appl. No. 13/181,729.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Mar. 6, 2013 for PCT/US2012/062738 which claims benefit of U.S. Appl. No. 13/288,459, filed Nov. 3, 2011.
Office Action from the U.S. Patent Office mailed Jul. 15, 2013 for U.S. Appl. No. 13/587,374.
Office Action from the U.S. Patent Office mailed Aug. 7, 2013 for U.S. Appl. No. 13/412,127.
Office Action from the U.S. Patent Office mailed Sep. 11, 2013 for U.S. Appl. No. 13/412,116.
US 6,238,418, 05/2001, Schwartz et al. (withdrawn)

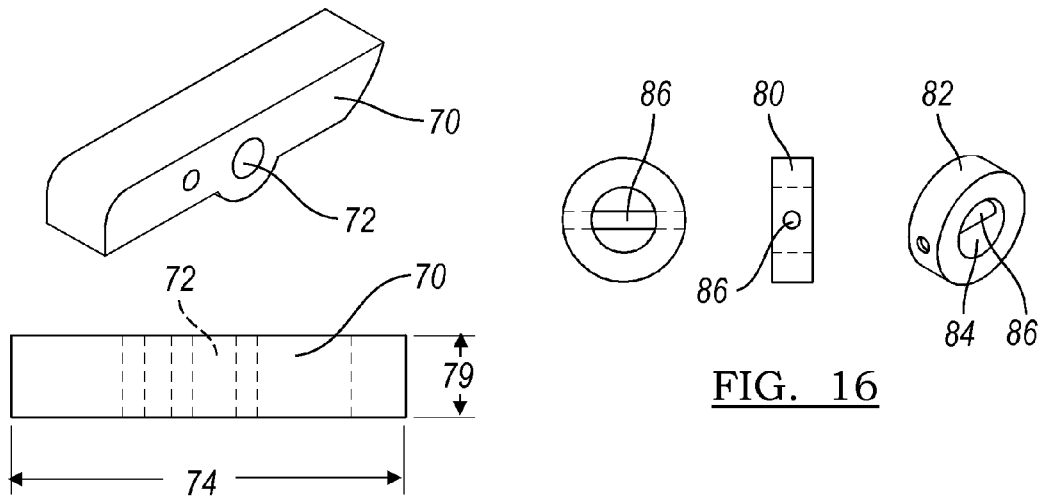
FIG. 14
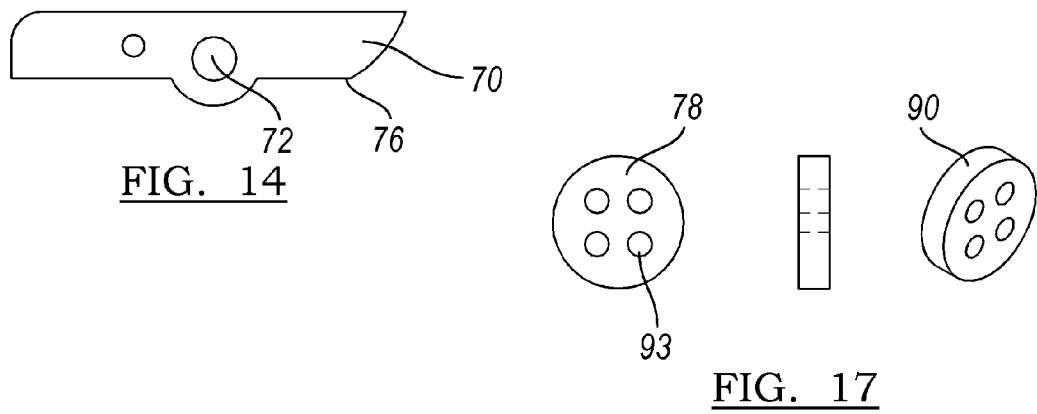
FIG. 16
FIG. 17
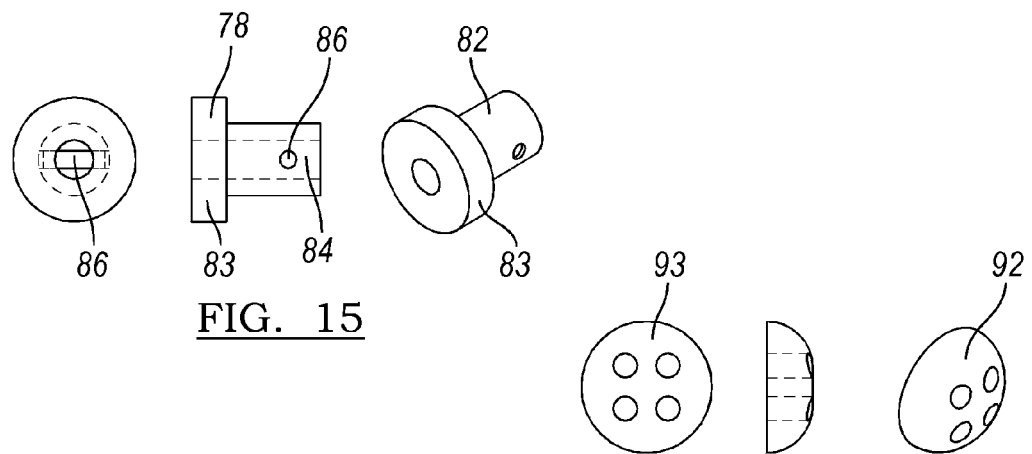
FIG. 15
FIG. 18

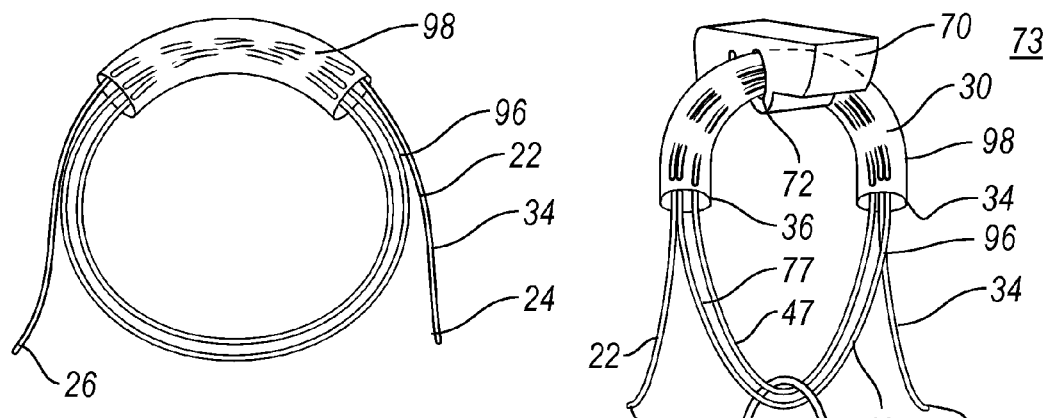
FIG. 20
FIG. 21
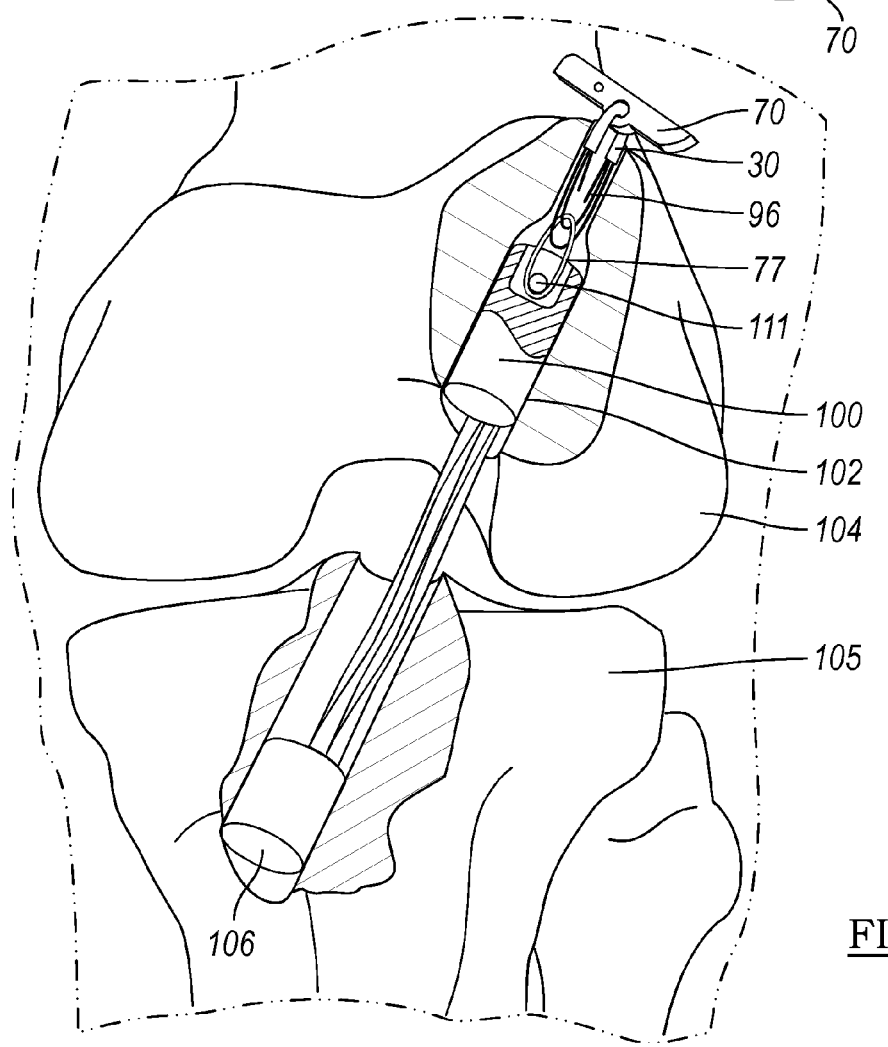
FIG. 22A

METHOD AND APPARATUS FOR COUPLING ANATOMICAL FEATURES

CROSS-REFERENCE TO RELATED APPLICATIONS

This application is a divisional of U.S. patent application Ser. No. 12/196,407 filed on Aug. 22, 2008, now U.S. Pat. No. 8,137,382, issued Mar. 20, 2012, which is a continuation-in-part application of: (1.) U.S. patent application Ser. No. 11/541,506 filed on Sep. 29, 2006, now U.S. Pat. No. 7,601,165 issued Oct. 13, 2009; (2.) U.S. patent application Ser. No. 12/014,399 filed on Jan. 15, 2008, now U.S. Pat. No. 7,909,851 issued Mar. 22, 2011; (3.) U.S. patent application Ser. No. 12/014,340 filed on Jan. 15, 2008, now U.S. Pat. No. 7,905,904 issued Mar. 15, 2011; (4.) U.S. patent application Ser. No. 11/935,681 filed on Nov. 6, 2007, now U.S. Pat. No. 7,905,903 issued Mar. 15, 2011; (5.) U.S. patent application Ser. No. 11/869,440 filed on Oct. 9, 2007, now U.S. Pat. No. 7,857,830 issued Dec. 28, 2010; (6.) U.S. patent application Ser. No. 11/784,821 filed on Apr. 10, 2007; (7.) U.S. patent application Ser. No. 11/347,661 filed on Feb. 3, 2006, now U.S. Pat. No. 7,749,250 issued Jul. 6, 2010; and (8.) U.S. patent application Ser. No. 11/347,662 filed on Feb. 3, 2006, now abandoned. The disclosures of the above applications are incorporated herein by reference.

FIELD

The present disclosure relates to a method and apparatus for stabilizing tissue and, more particularly, to a method of coupling soft tissue to a bone and for stabilizing anatomical features.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single pre-formed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction into a tunnel formed in a bone is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. The first and second ends and the first and second loops are then passed through the tunnel. Soft tissue is then passed through the first and second loops. Tension is applied onto the first and second ends to constrict the first and second loops about the soft tissue.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled to at least one of the first and second loops. After the fastener is coupled to the patient, tension is applied onto the first and second ends to constrict at least one of the first and second loops.

In another embodiment a method of surgically implanting a soft tissue replacement for attaching two bone members is disclosed. First and second tunnels are formed in first and second bones. A pair of locking members having a first profile which allows insertion of the locking members through the tunnel and a second profile which allows engagement with the positive locking surface upon rotation of the locking members is provided. The suture construction described above is coupled to the locking members. The first and second ends and the first and second loops of the construction and the locking member are threaded through the first and second tunnels. Tension is applied to the suture construction to engage the locking members and pull the first and second bones together.

In another embodiment an assembly for coupling a first portion of an anatomy to a second portion of the anatomy is disclosed. The assembly includes an anchor having an anchor body and a first and second bores through the anchor body. A first adjustable suture construct having a body portion passes through the first bore of the anchor and includes first and second adjustable loops slidable relative to a passage portion defined in the body portion of the first adjustable suture construct. A similar second adjustable suture construct passes through the second bore of the anchor.

In another embodiment, a method of coupling a first portion of an anatomy to a second portion of the anatomy is disclosed. The method includes forming a first bore in a first bone of the anatomy, forming a second bore in a second bone of the anatomy, and positioning a first anchor relative to the first bore. A second anchor is positioned relative to the second bore. First and second adjustable suture constructs extend from the second anchor. Each of the first and second adjustable suture constructs have corresponding body portions and are positioned between the first and second bones. The first and second adjustable suture constructs are coupled with corresponding first and second ligament replacements. At least one end of the first adjustable suture construct is tensioned to tension the first ligament replacement and adjust a size of first and second adjustable loops slidably passing through a longitudinal interior bore defined in a passage portion of the body portion of the first adjustable suture construct. Similarly, at least one end of the second adjustable suture construct is tensioned to tension the second ligament replacement.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 14-18 represent fasteners used in the teaching herein;

FIGS. 20 and 21 represent suture constructions;

FIGS. 22A through 22D represent the use of the suture construction of FIG. 21 to couple a soft tissue construction to a femoral/humeral tunnel;

DETAILED DESCRIPTION

Figure 1:
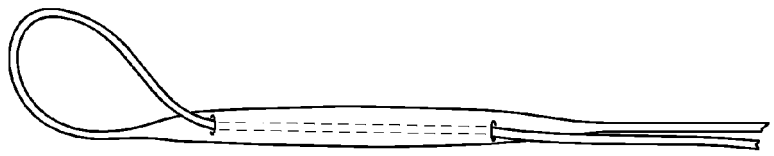
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
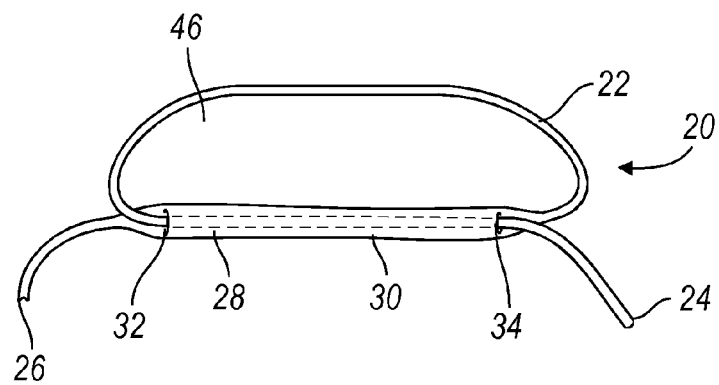
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
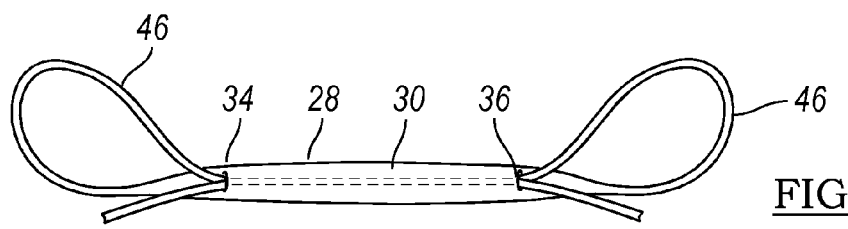
Figure 3:
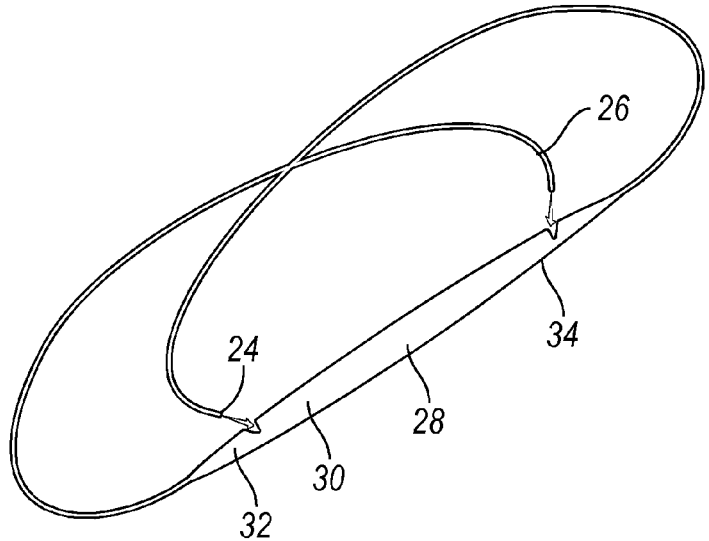
FIG. 3 represents the formation of the suture configuration shown in FIG. 2A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture 22 once it is tightened.

The first and second apertures are formed during the braiding process as loose portions between pairs of fibers defining the suture 22. As further described below, the first and second ends 24 and 26 can be passed through the longitudinal passage 30 multiple times. It is envisioned that either a single or multiple apertures can be formed at the ends of the longitudinally formed passage.

Figure 4A:
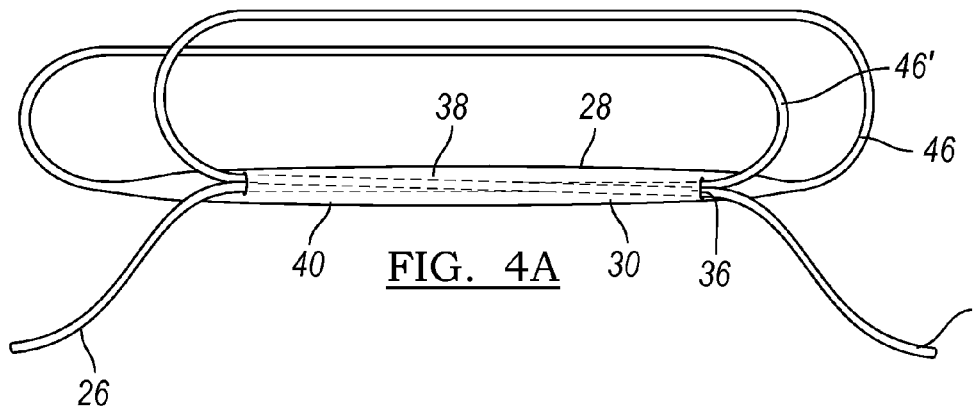
FIGS. 4A and 4B represent alternate suture configurations.
Figure 4B:
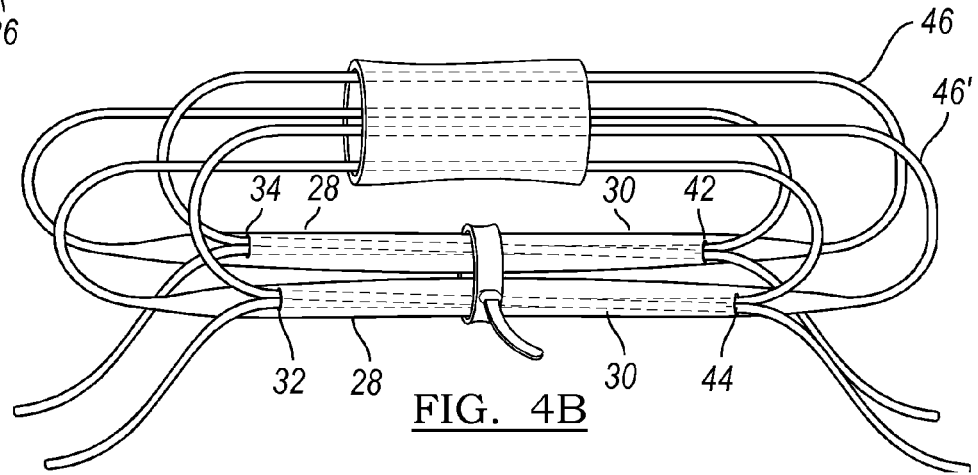

As best seen in FIGS. 4A and 4B, a portion of the braided body 28 of the suture 22 defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
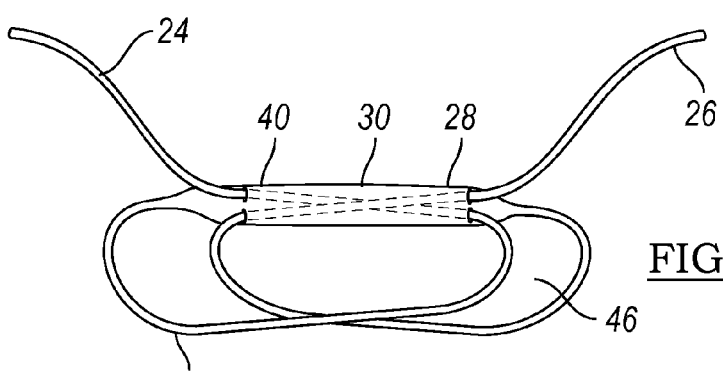
FIGS. 5-7 represent further alternate suture configurations.
Figure 6:
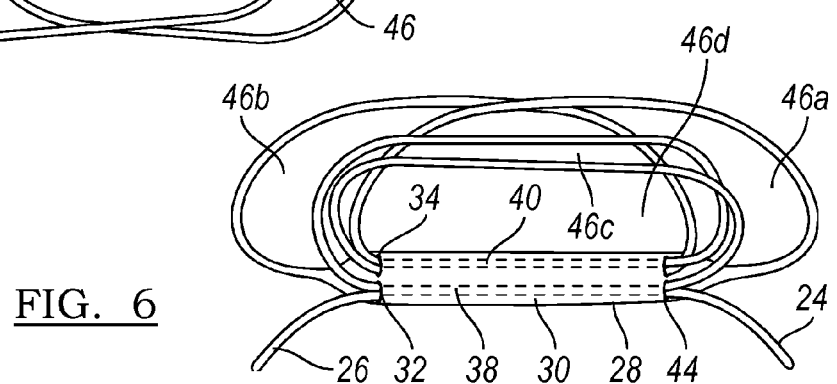
Figure 7:
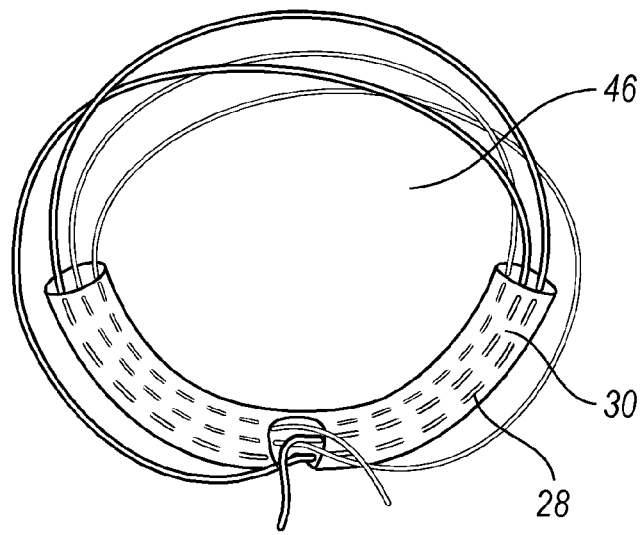
Figure 8:
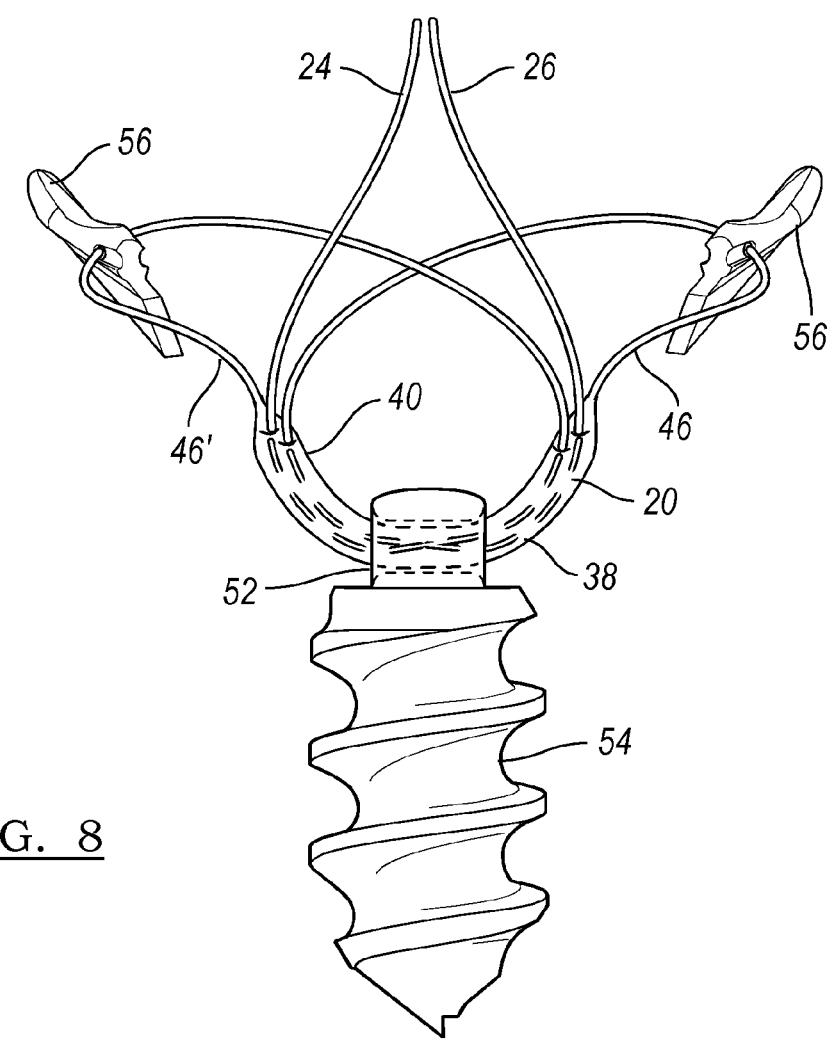
FIG. 8 represents the suture construction according to FIG. 5 coupled to a bone engaging fastener.
Figure 9:
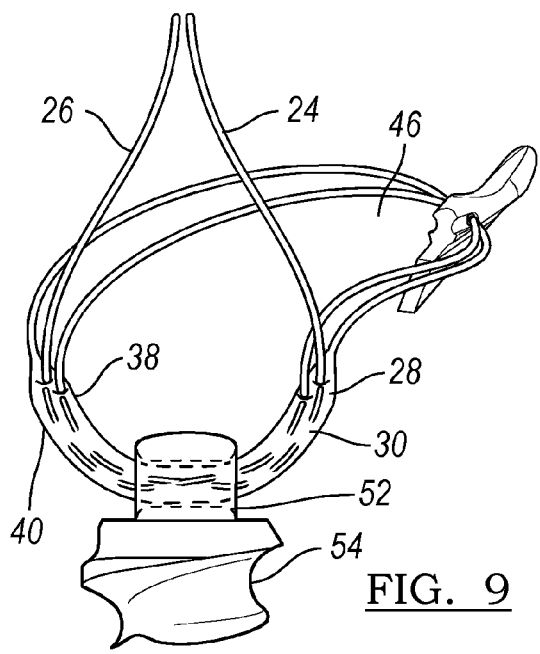
FIGS. 9-11B represent the coupling of the suture construction according to FIG. 5 to a bone screw.
Figure 10:
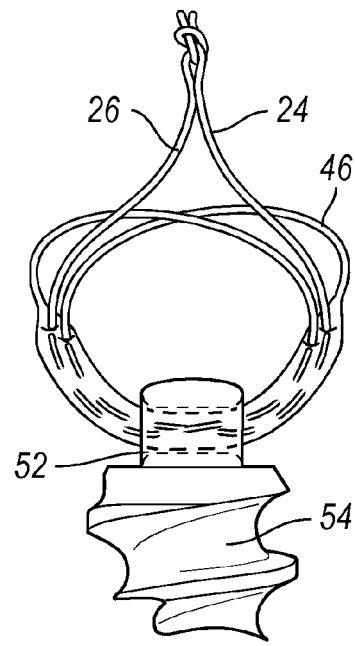

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture 22 with respect to each other.

Upon applying tension to the first and second ends 24 and 26 of the suture 22, the size of the loops 46a-d is reduced to a desired size or load. At this point, additional tension causes the body of the suture 22 defining the longitudinal passage 30 to constrict about the parallel portions of the suture 22 within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
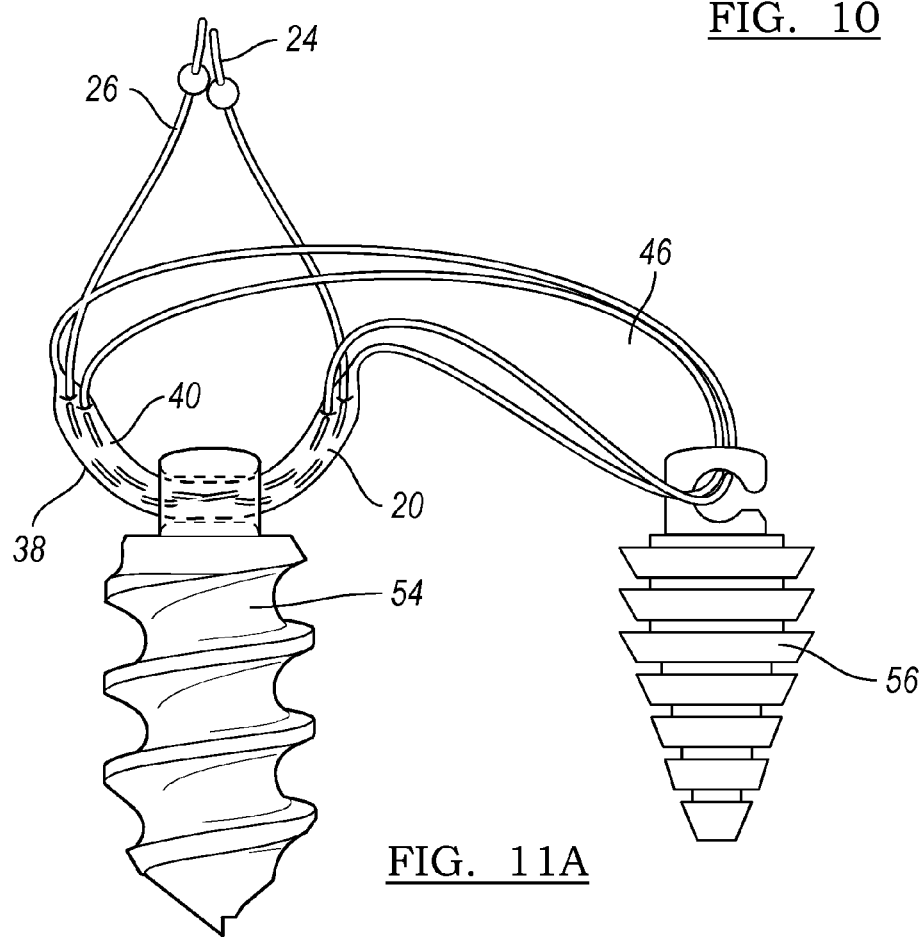
Figure 11B:
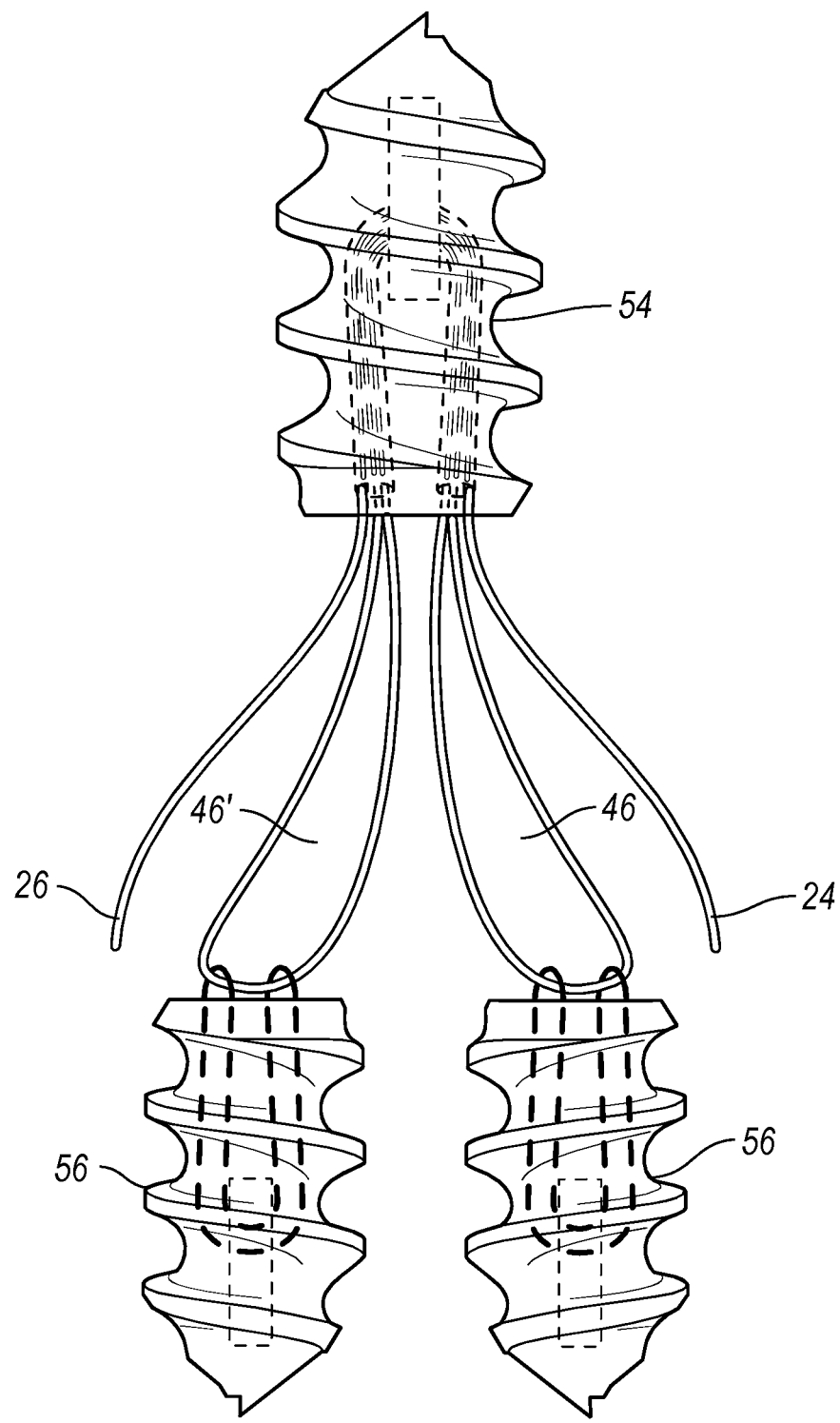

FIG. 11b represents the coupling of the suture construction according to FIG. 2B with a bone fastening member. Coupled to a pair of loops 46 and 46' is tissue fastening members 56. The application of tension to either the first or second end 24 or 26 will tighten the loops 46 or 46' separately.

Figure 12A:
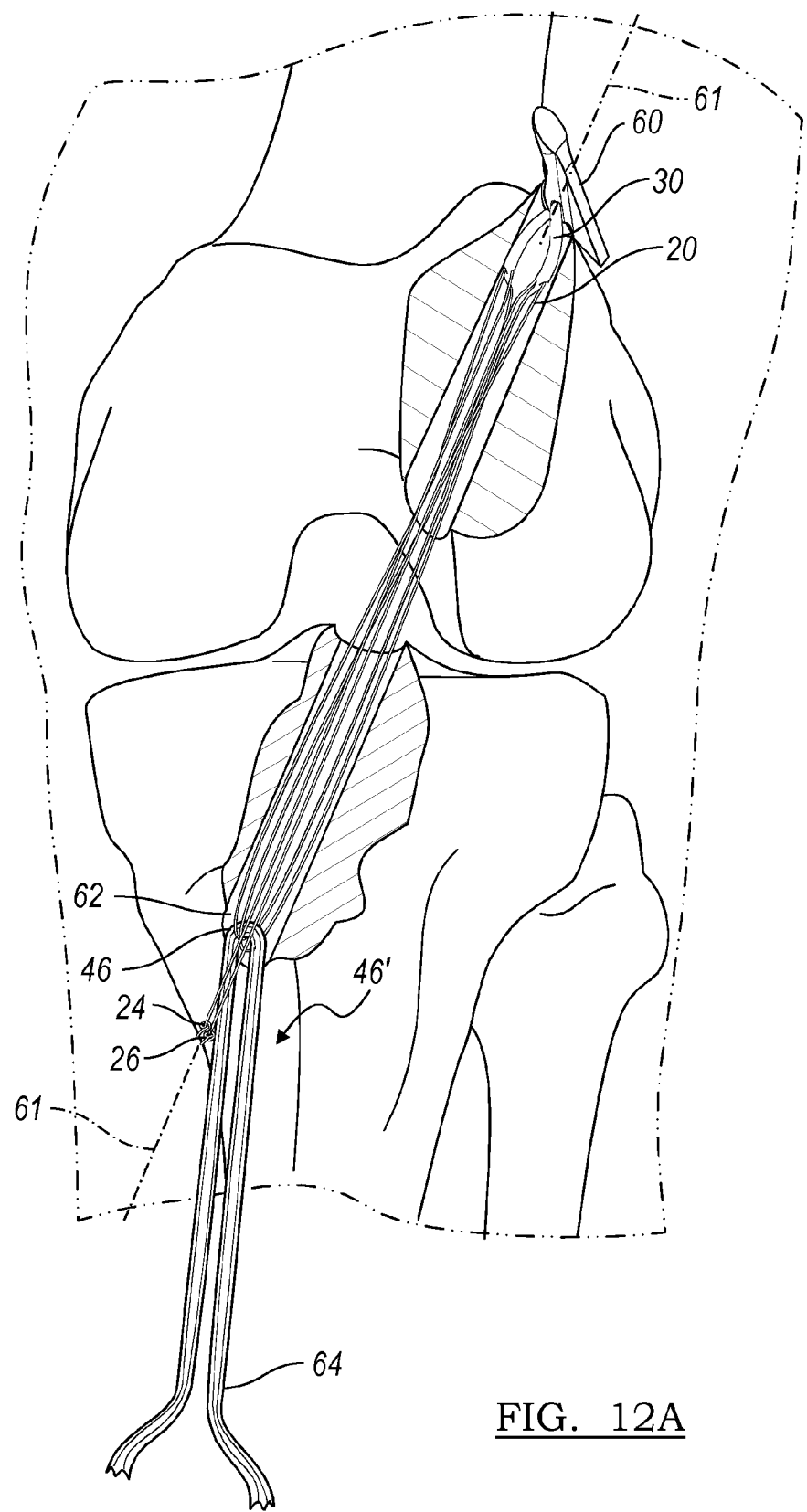
FIGS. 12A-12E represent the coupling of a soft tissue to an ACL replacement in a femoral/humeral reconstruction.

FIGS. 12A-12E represent potential uses of the suture constructions 20 in FIGS. 2A-7 in an ACL repair. As can be seen in Figure 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

Figure 12B:
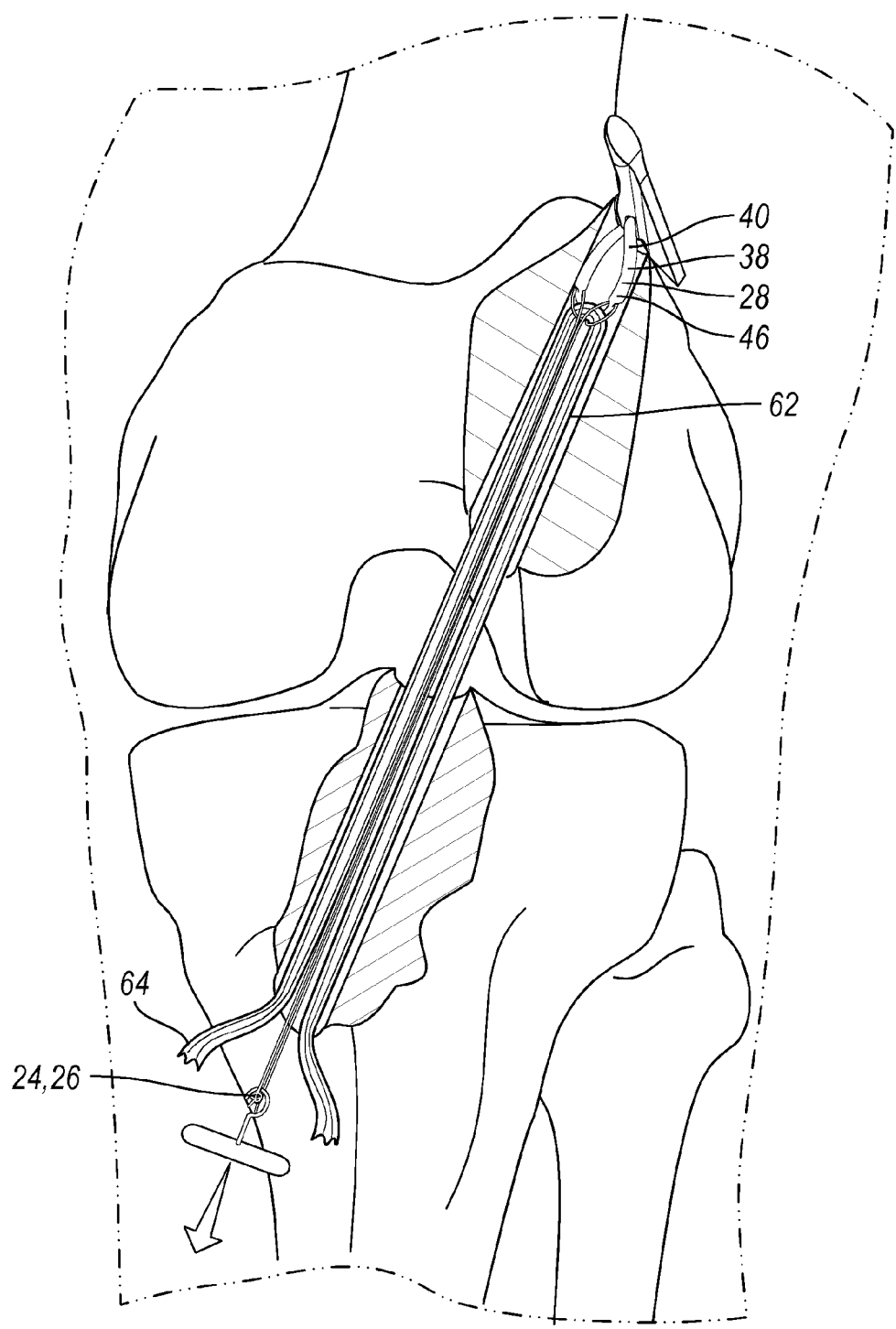
Figure 12C:
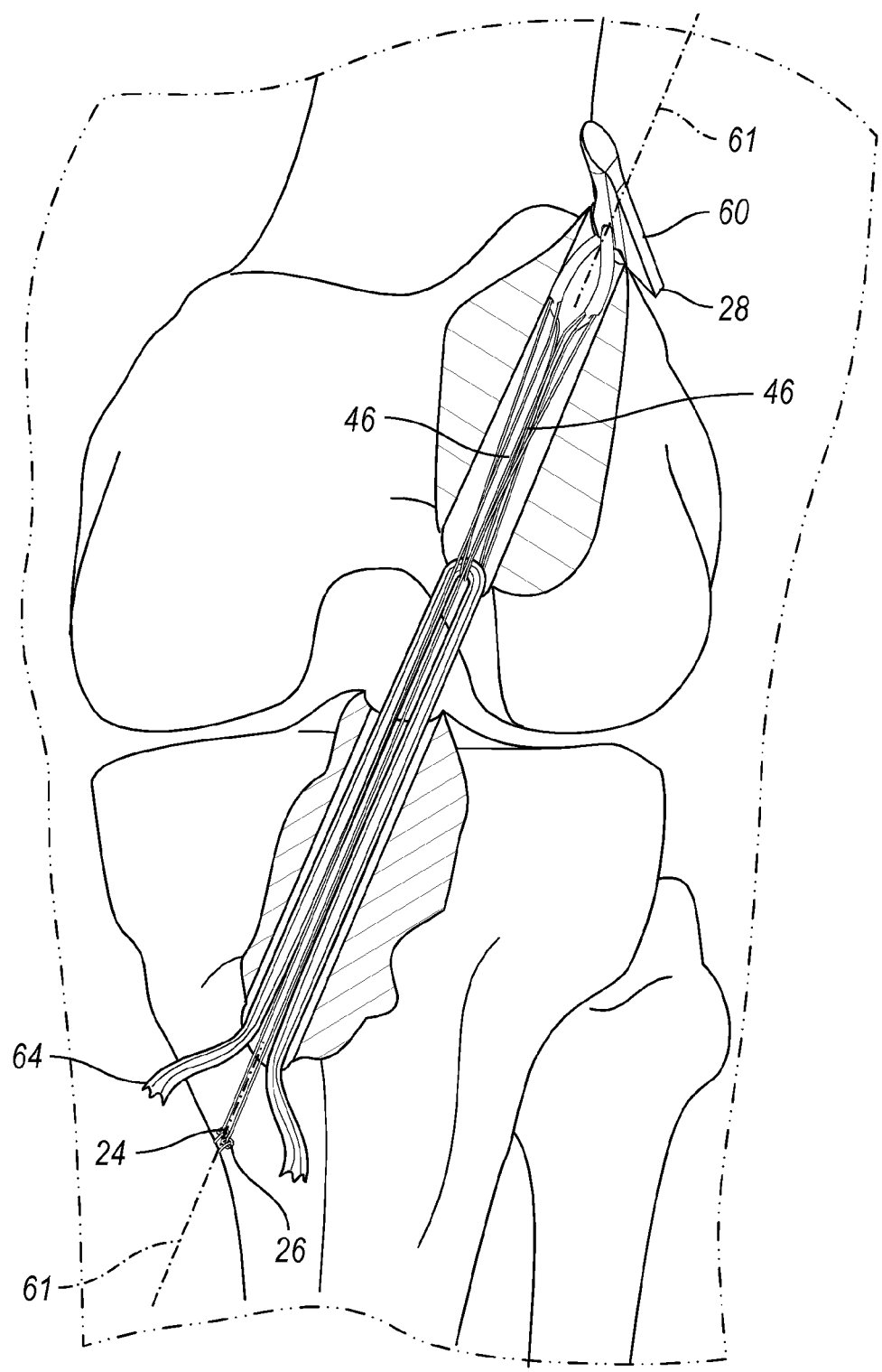
Figure 12D:
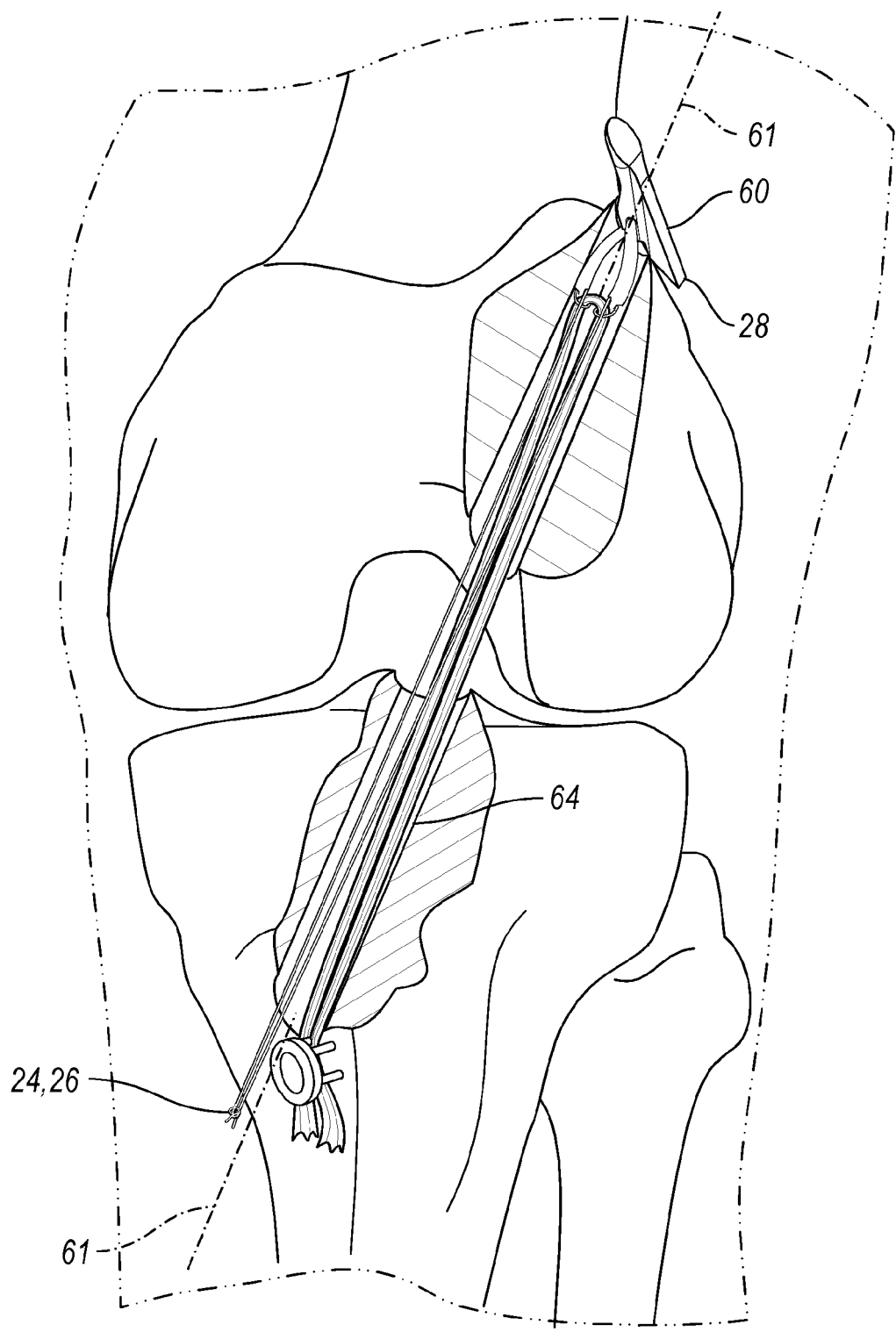

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
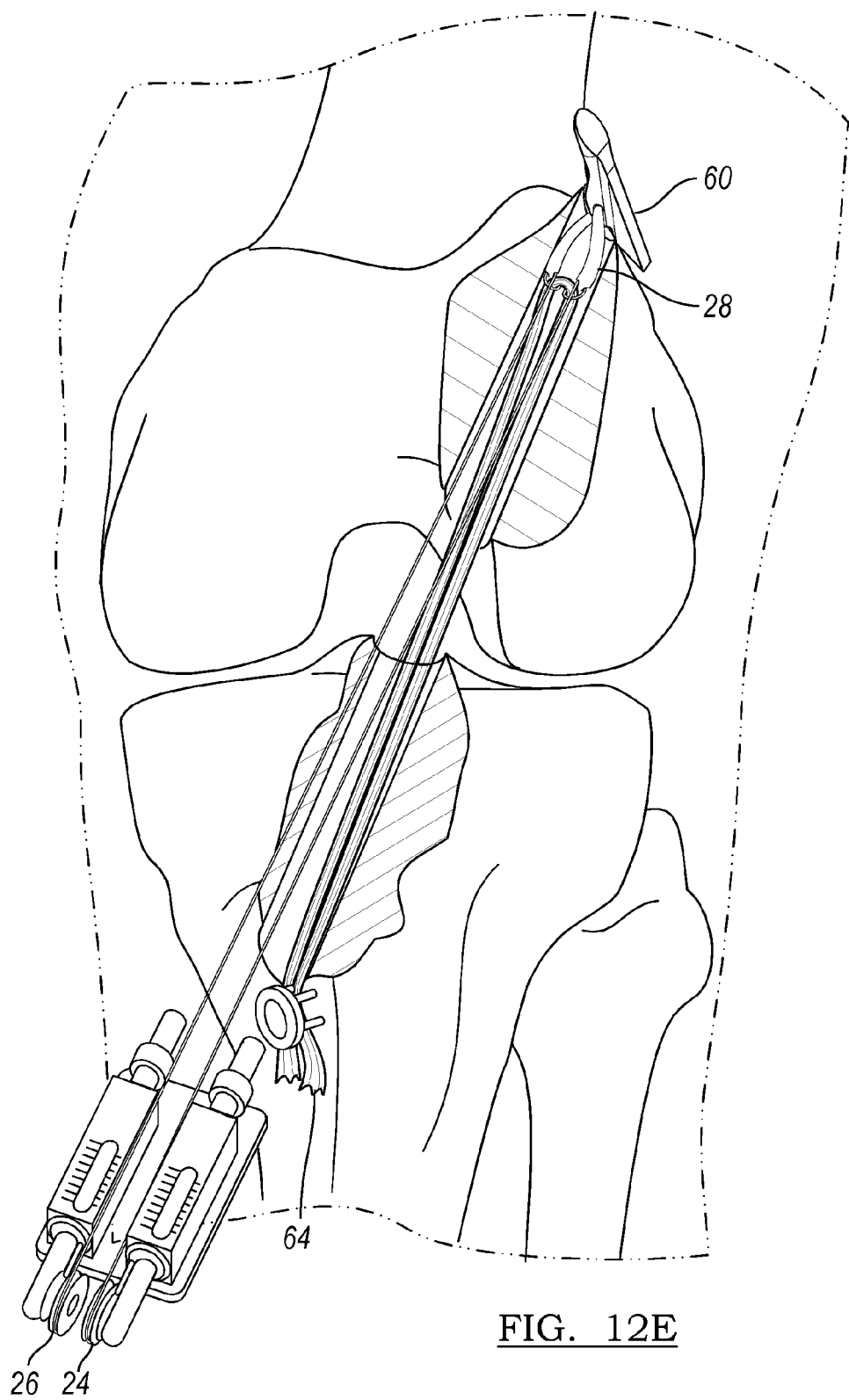
Figure 13A:
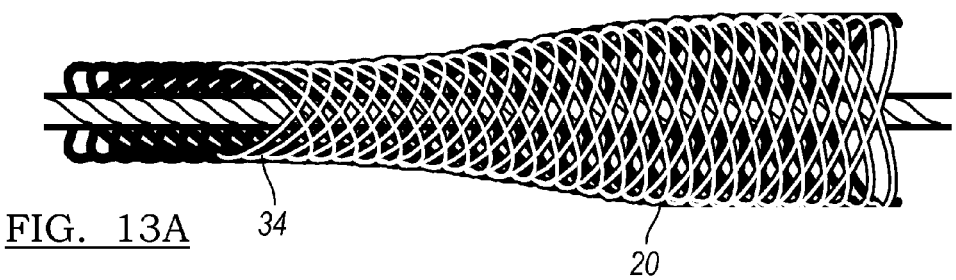
FIGS. 13A-13D represent a close-up view of the suture shown in FIGS. 1-11C.
Figure 13B:
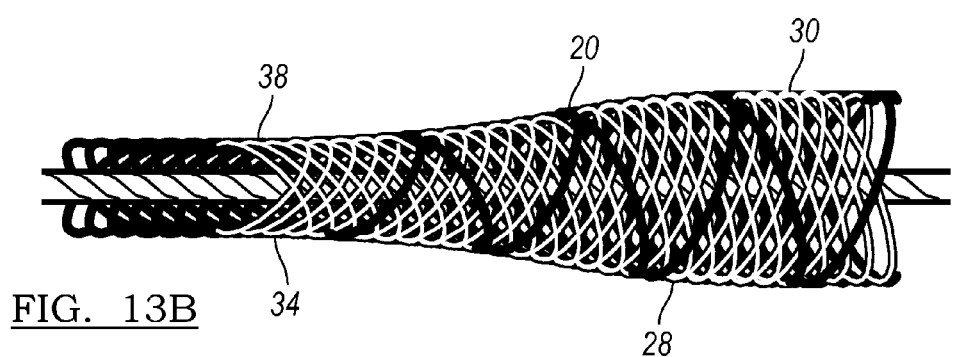
Figure 13C:
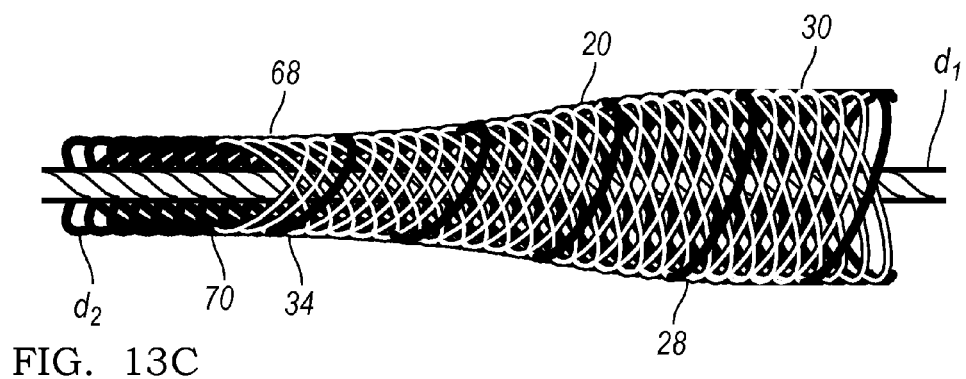
Figure 13D:
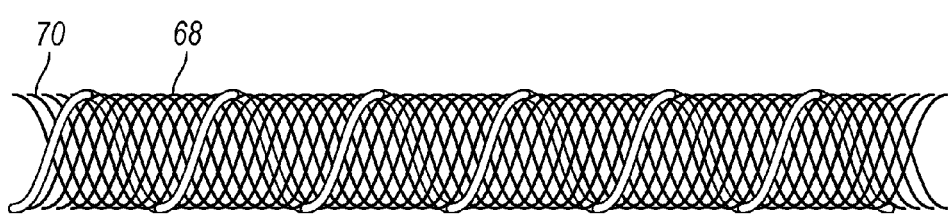

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

FIGS. 14-18 represent various fasteners which can be used with the suture constructions of FIGS. 1-7. FIG. 14 represents an elongated anchor 70 defining a suture accepting bore 72. As described below, the anchor 70 has a first profile 79 which allows the anchor 70 to be passed through a bore defined in a bone. The anchor 70 can be rotated so as to have a second profile 74 to allow engagement with a patient. The fastener 70 has a tissue engaging surface 76 which is configured to engage either soft tissue or bone. Examples of this can be found in the form of a toggle lock in co-assigned and co-pending U.S. patent application Ser. No. 10/864,900, incorporated herein by reference.

As shown in FIGS. 15 and 16, the fasteners 78 and 80 can have a generally cylindrical body 82 defining a through bore 84. Disposed across the through bore 84 is a transverse pin 86 which is configured to slidably bear the suture construction. Optionally, the fastener can have an outer engagement rib or flange 83 which is configured to engage the periphery of an aperture formed in the bone. The cylindrical body 82 can have an outside diameter which is less than the diameter of the bore in the bone.

As shown in FIGS. 17 and 18, the fasteners 90 and 92 can have a general planar button configuration having a plurality of suture accepting through bores 93. These bores 93 can slidably or fixably accept the suture 22. The button can have a diameter greater than the diameter of the tunnel formed in the bone. It is envisioned the fasteners 90 and 92 can have flat or curved bearing surfaces. In this regard, the bearing surface of the fasteners 90 and 92 can have a convex bearing shape.

Figure 19:
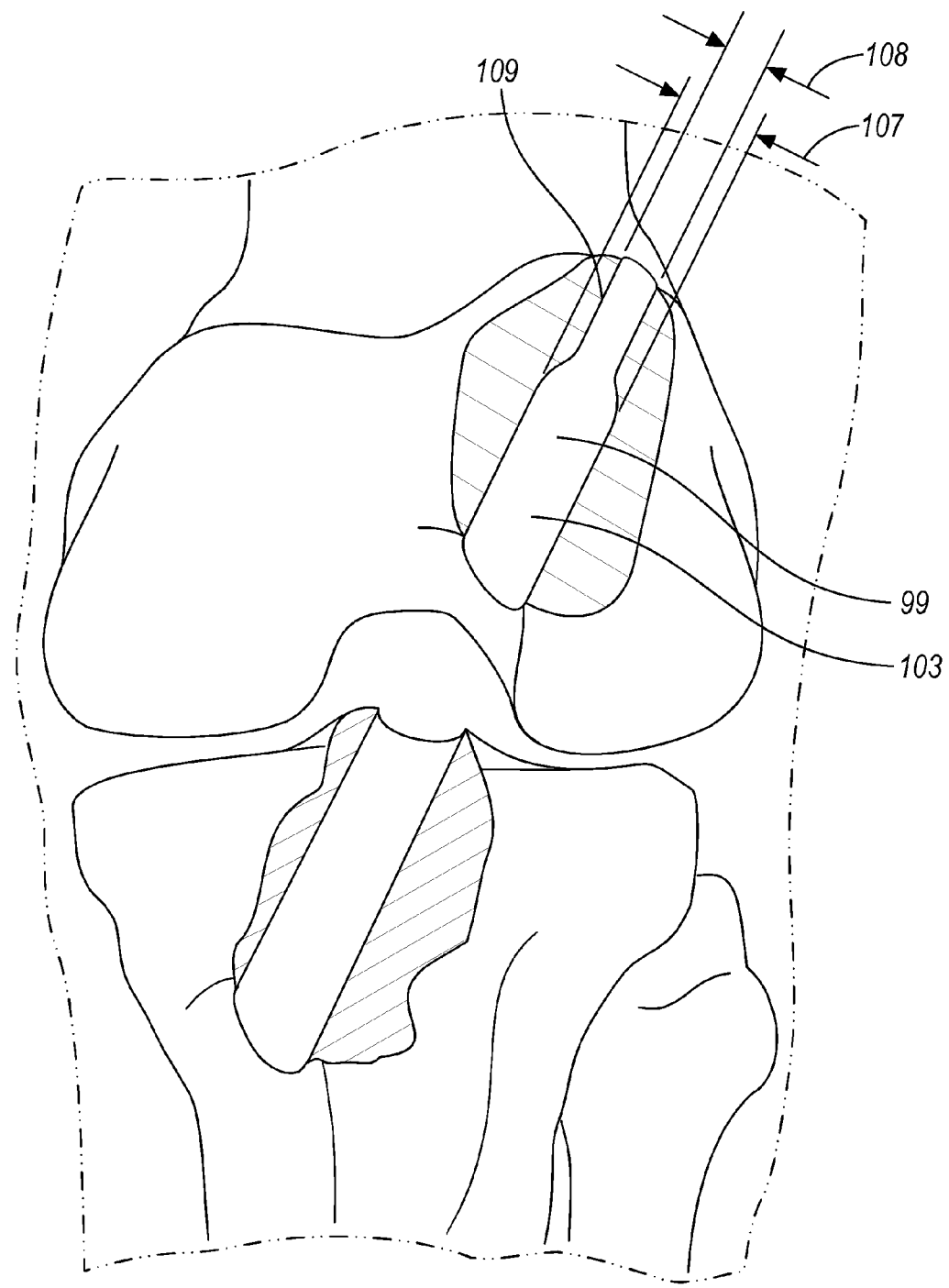
FIG. 19 represents the preparation of the femoral and humerus according to the teachings herein.

FIGS. 19-22B represent the use of the suture construction to couple a bone-tendon-bone graft construction 100 within a femoral/tibial tunnel 102. As shown in FIG. 19, the tunnel 99 can have a first portion 103 with a first diameter 107 and a second portion 109 having second smaller diameter 108 within the femur. As described below, the second diameter 108 can be used to couple the bone-tendon-bone construction 100 to the tunnel.

As shown in FIGS. 20 and 21, a loop of suture 96 is passed through a collapsible tube 98. The collapsible tube or a pair of loops formed by a suture 22 is positioned within the bore 72 of a first fastener 70. As described above, the collapsible tube 98 can be a portion of the suture 22, or can be a separate member.

As seen in FIG. 21, to form the suture construction 73, the suture 22 is passed through the first bore 72 defined by the first fastener 70. The suture 22 can then be passed through a second bore defined by a second fastener 70 or a suture loop 77. In any of the embodiments, the collapsible tube 98 can be a portion of the suture. A first end 26 of the suture 22 is passed through a first aperture 34 defined by the collapsible tube 98 into a passage portion 30 defined by the collapsible tube 98 and out a second aperture 36 defined by the collapsible tube 98 so as to place the first end outside of the passage portion 30 and form a first loop. A second end 26 of the suture 22 is passed through the second aperture 36 into the passage portion 30 and out the first aperture 34 so as to place the second end 26 outside of the passage portion 30 and form a second loop 47. At this point, the passage portion 30 can optionally be positioned within the first bore 72 of the fastener 70 or the loop of the suture 22.

Figure 22B:
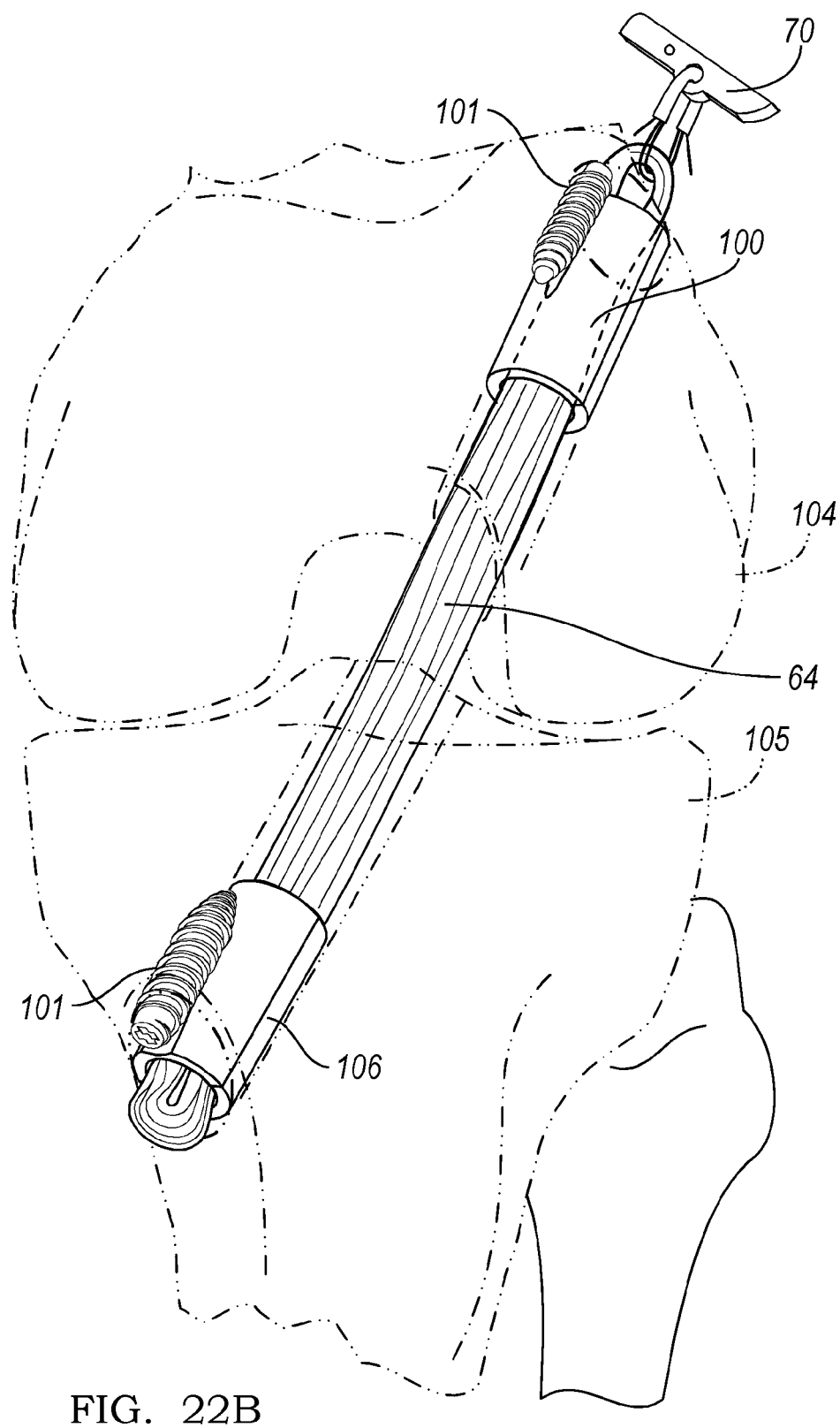

As seen in FIG. 22A and 22B, the construction 73 is coupled to a bone-tendon-bone construction 100 using the loop of suture 77 or a fastener. The bone-tendon-bone implant 100 can be formed of an allograph-tendon construction or artificial bone-tendon or bone-tendon-bone prosthetic assembly. It is envisioned the physician can intraoperatively determine the desired graft or graft assembly length and appropriate graft tension.

After fixing the suture construction to the bone-tendon-bone construction 100 by for example a through pin 111, the bone-tendon-bone construction 100 is installed into the tunnel 102 formed in a femur and tibia 104, 105. As described above with respect to FIG. 12A, the suture construction 73 of FIG. 21 can be fed through the femoral tunnel 102. The bone-tendon-bone construction 100 is then put into the tunnel 102. A first portion 106 of the bone-tendon-bone construction 100 is coupled to a tibial tunnel using a fastener 101 positioned within the tunnel. A second portion of the bone-tendon-bone construction 100 is pulled taught into the femoral tunnel by tensioning the ends 24 and 26 of the suture construction 73. The portion 113 of the bone-tendon-bone construction 100 can be coupled to the femur using a transverse or parallel bone engaging screw 101.

Figure 22C:
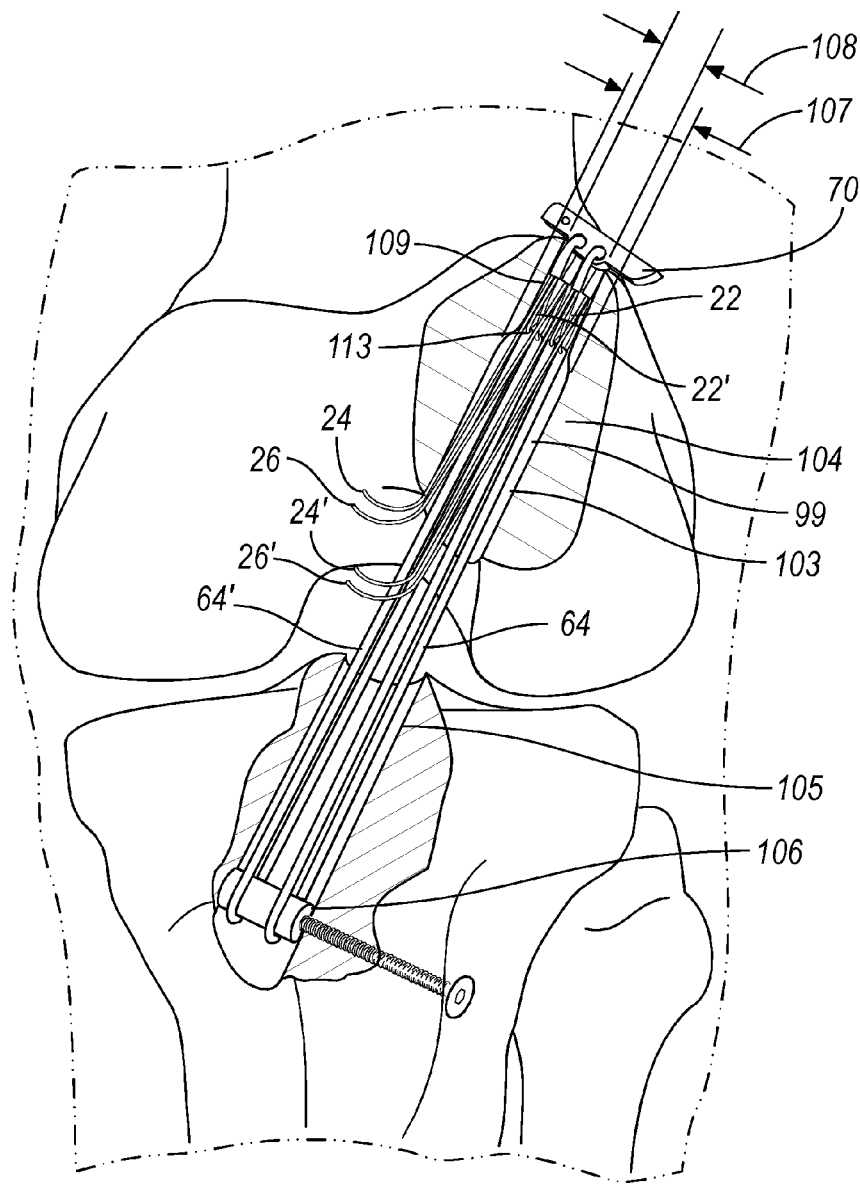
Figure 22D:
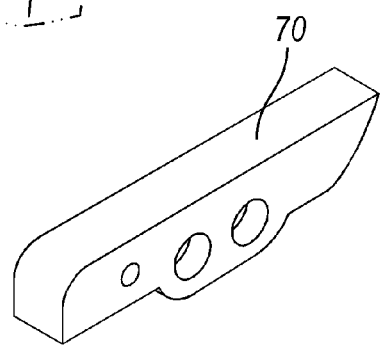

As seen in FIG. 22C and 22D, a pair of suture constructions 22 and 22' are coupled to a pair of soft tissue replacements 64 and 64' using the loops of suture 77, 77' or a fastener. The pair of soft tissue replacements 64 and 64' can be formed of artificial of harvested tendon material. It is envisioned the physician can intraoperatively determine the desired graft or graft assembly length and appropriate graft tension.

After fixing the suture constructions 22 and 22' to a toggle lock (see FIG. 22D) and the pair of soft tissue replacements 64 and 64' are implant into the tunnel 102 formed in a femur and tibia 104, 105. As described above with respect to FIG. 12A, the suture constructions 22 and 22' of FIG. 21 can be fed through the femoral tunnel 104. The pair of soft tissue replacements 64 and 64' are then pulled into the tunnel 104 by applying tension onto the ends 24-26' of the suture constructions. A first portion 106 of the pair of soft tissue replacements 64 and 64' is coupled to a tibial tunnel 105 using a fastener 101 such as a WASHERLOK™ tibial fixation as provided by Biomet Sports Medicine positioned within the tunnel. A second portion of the pair of soft tissue replacements 64 and 64' is pulled taught into the femoral tunnel by tensioning the ends 24 and 26 of the suture construction 73. The portion 113 of the pair of soft tissue replacements 64 and 64' can be coupled to the femur using a transverse or parallel bone engaging screw 101. It is envisioned the suture ends 24 and 26 can be passed though a medial portal 25 to facilitate the tensioning of the pair of soft tissue replacements 64 and 64.

Alternatively, after insertion into the femoral tunnel 102, as seen in FIG. 12B, an appropriate amount of tension is applied to the pair of soft tissue replacements 64 and 64' by applying tension to the ends 24 and 26 of the suture construction. A fastener 101 is engagably driven between the ends of pair of soft tissue replacements 64 and 64' and the internal surface of the bore formed in the tibia. This locks the pair of soft tissue replacements 64 and 64' to the bone.

Figure 23:
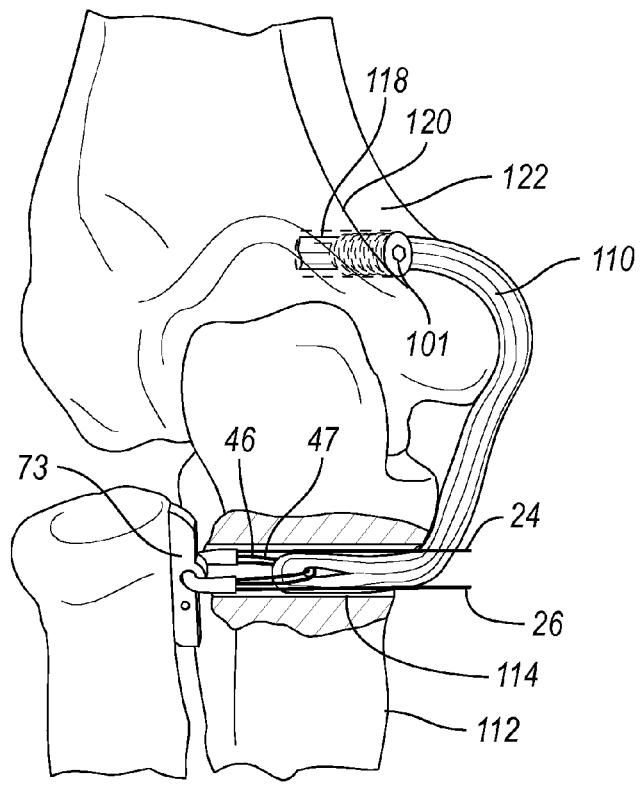
FIGS. 23 and 24 represent the coupling of soft tissue to an ulna.

FIG. 23 represents the coupling of a flexor tendon 110 to the humerus. Shown is the ulna 112 having a through bore 114. The through bore 114 can accept the suture construction 73 shown in FIG. 21. As described above with respect to the ACL replacement shown in FIG. 12A, the suture construction 73 is fed through the tunnel 114 formed in the ulna 112. A soft tissue graft 110 is fed through the pair of loops 46, 47 formed by the suture construction 73. The ends 24, 26 of the suture 22 are then pulled so as to pull the soft tissue graft 110 to or into the tunnel 114. A second end of the soft tissue graft 118 can be coupled to a bore 120 formed in a lateral epicondyle 122 of the humerus. A soft tissue engaging fastener 101 can be used to couple a soft tissue 110 to the bore 120. After engagement of the soft tissue fastener 101, the tension of the soft tissue 110 can be adjusted by the tensioning of the suture construction 73.

Figure 24:
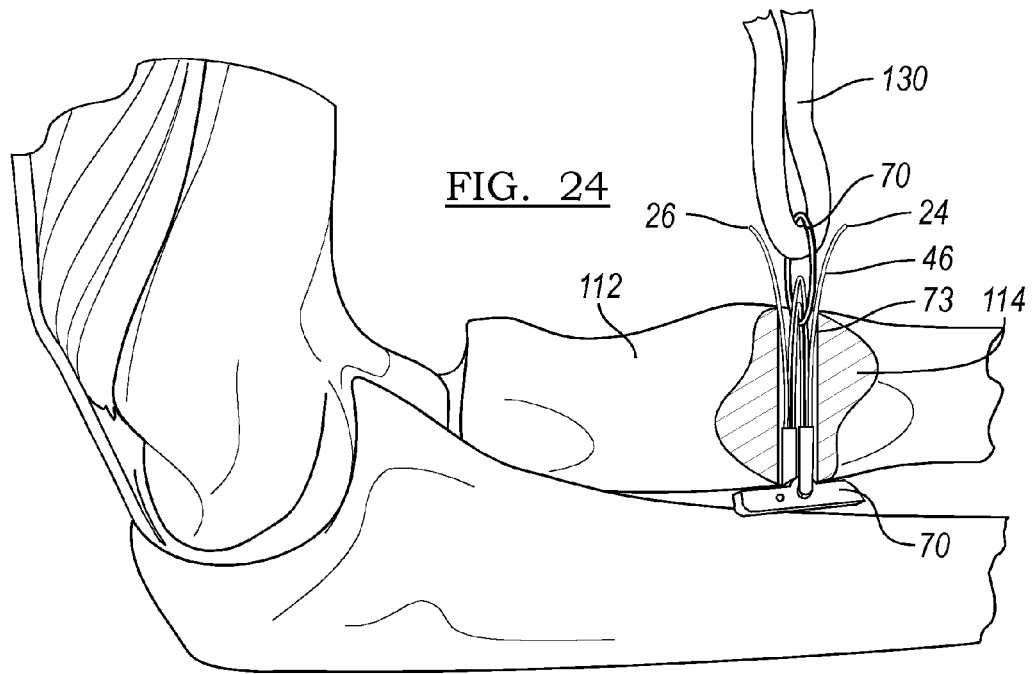

Similarly, as shown in FIG. 24, the bicep brachii tendon 130 can be coupled to the ulna 112 using the suture construction 73 shown in FIG. 21. In this regard, a bore 114 is formed in the ulna. The fixation member 70 is then positioned or coupled to the ulna 112. At this point, a natural or artificial bicep brachii tendon 130 can be passed through a loop or second fastener 70 or the loops 46, 47 formed in the suture construction 73. Tensioning of the first and second ends 24 and 26 applies tension to the loops 46, 47, thus pulling the tendon 64 to or into the bore 114. The constricting the loops 46,47 then fasten the bicep brachii tendon 130 to the ulna 112. It is envisioned a bone coupling fastener 101 can be used to fix the soft tissue 130 to the ulna.

Figure 25:
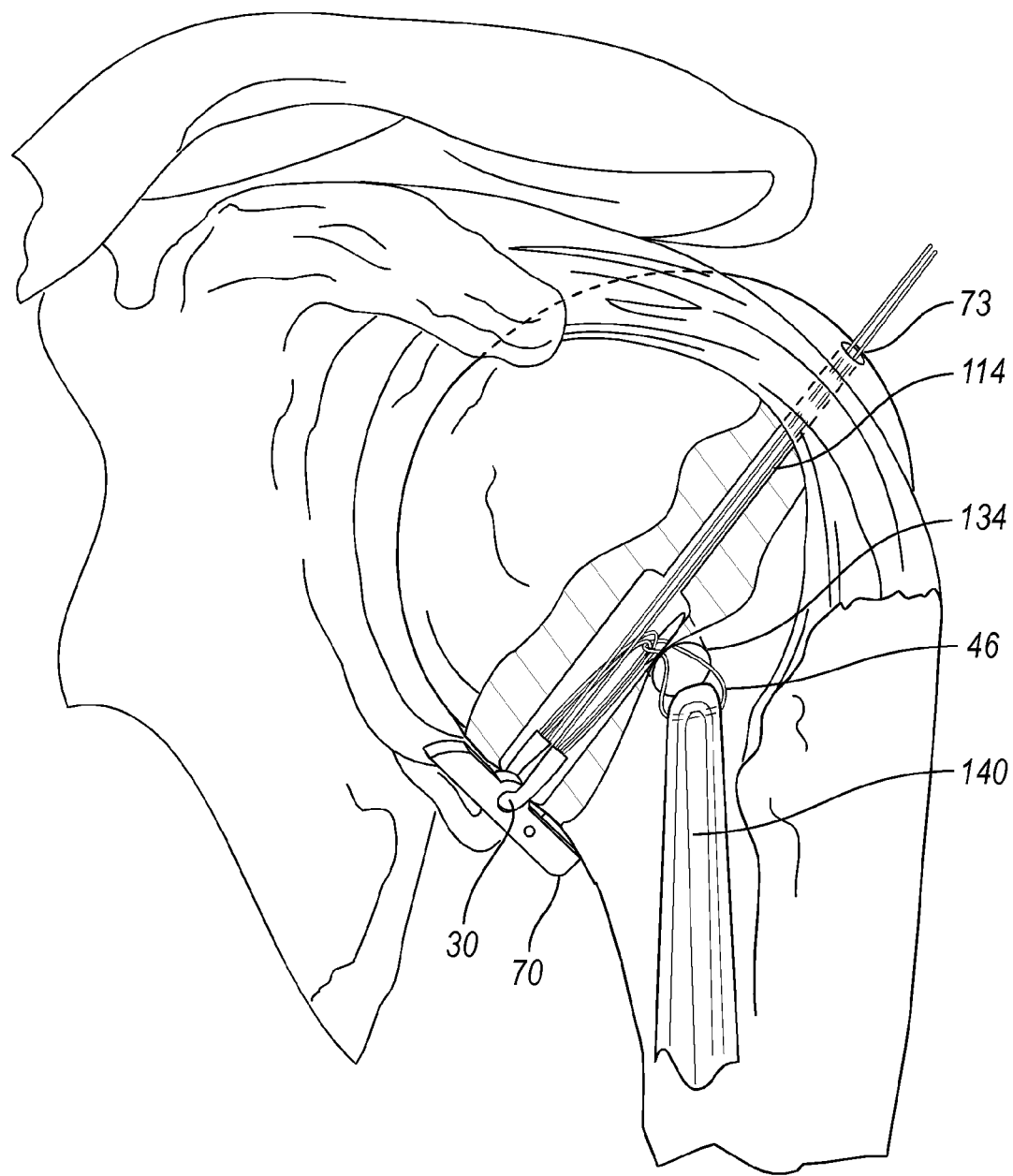
FIG. 25 represents the coupling of soft tissue to a humerus.

FIG. 25 shows the coupling of soft tissue 140 to the head of the humerus. Defined in the humerus is a bore 114 configured to support the suture construction 73. This bore can further have a transverse passage 134. The transverse passage 134 can have at least one loop of the suture construction 73 disposed therethrough so as to allow the coupling of soft tissue to or through the transverse passage 134. The longitudinal passage portion 30 of suture construction 73 can be first coupled to a fixation member 70. The member 70 has a first profile which allows insertion of the member 70 through the tunnel and a second profile which allows engagement with a positive locking surface upon rotation. The longitudinal passage portion 30 of the suture construction 73, member 70, loops 46 and ends 24, 26 can then be passed through the tunnel.

The fixation member 70 is positioned or coupled to the humeral head. At this point, a natural or artificial bicep tendon 140 can be passed through a loop or loops formed in the suture construction 73. Tensioning of the first and second ends 24 and 26 applies tension to the loops, thus pulling the tendon 140 to or into the transverse passage 134. In this regard, the first and second ends are pulled through the tunnel 114, thus constricting the loops about the tendon 140 and pulling the tendon 140 or soft tissue to the transverse tunnel 134. Optionally, a soft tissue fastening screw can be used to fix the tendon 140 to the transverse passage 134.

Figure 26:
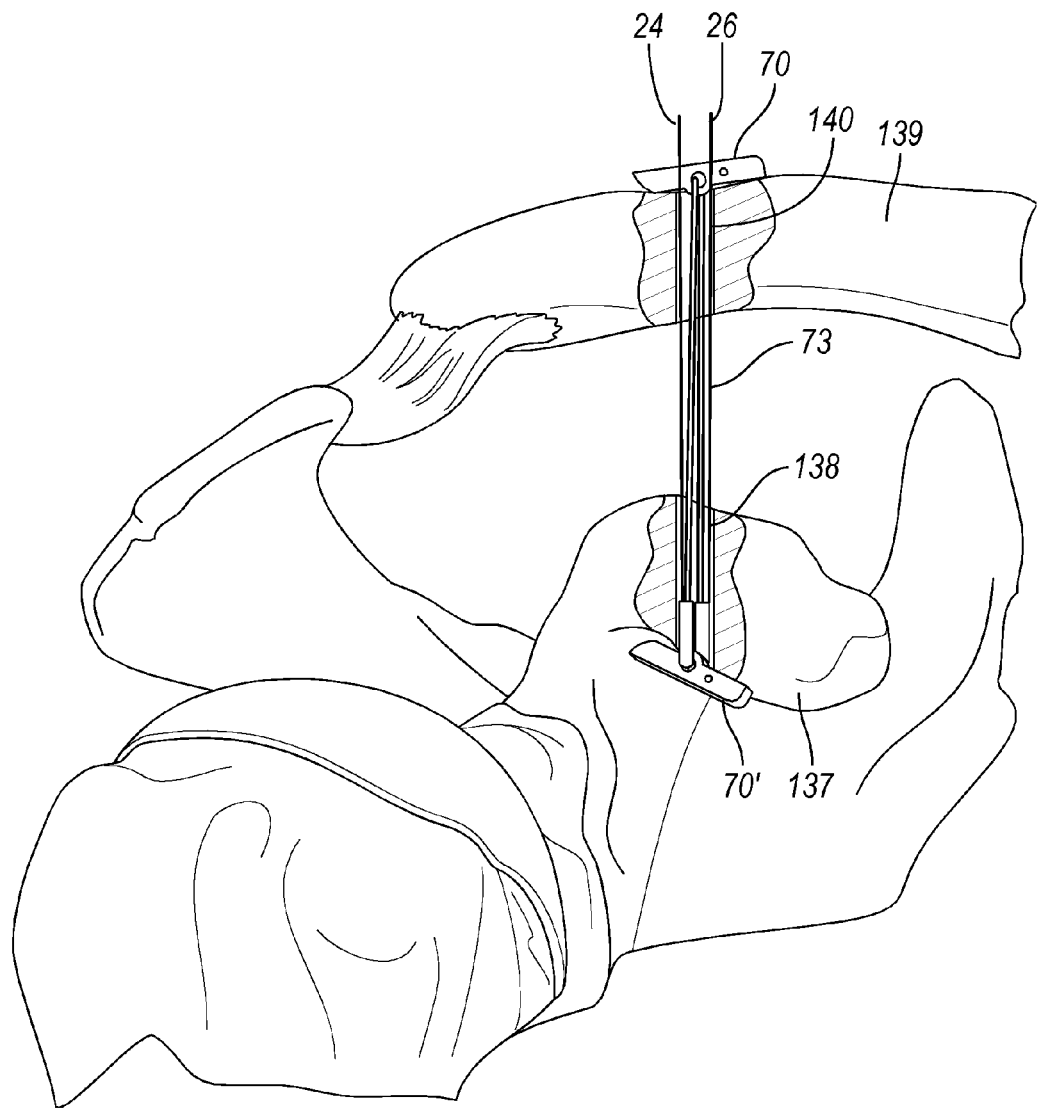
FIGS. 26-28 represent the stabilization of bony structures utilizing suture constructions taught herein.
Figure 27:
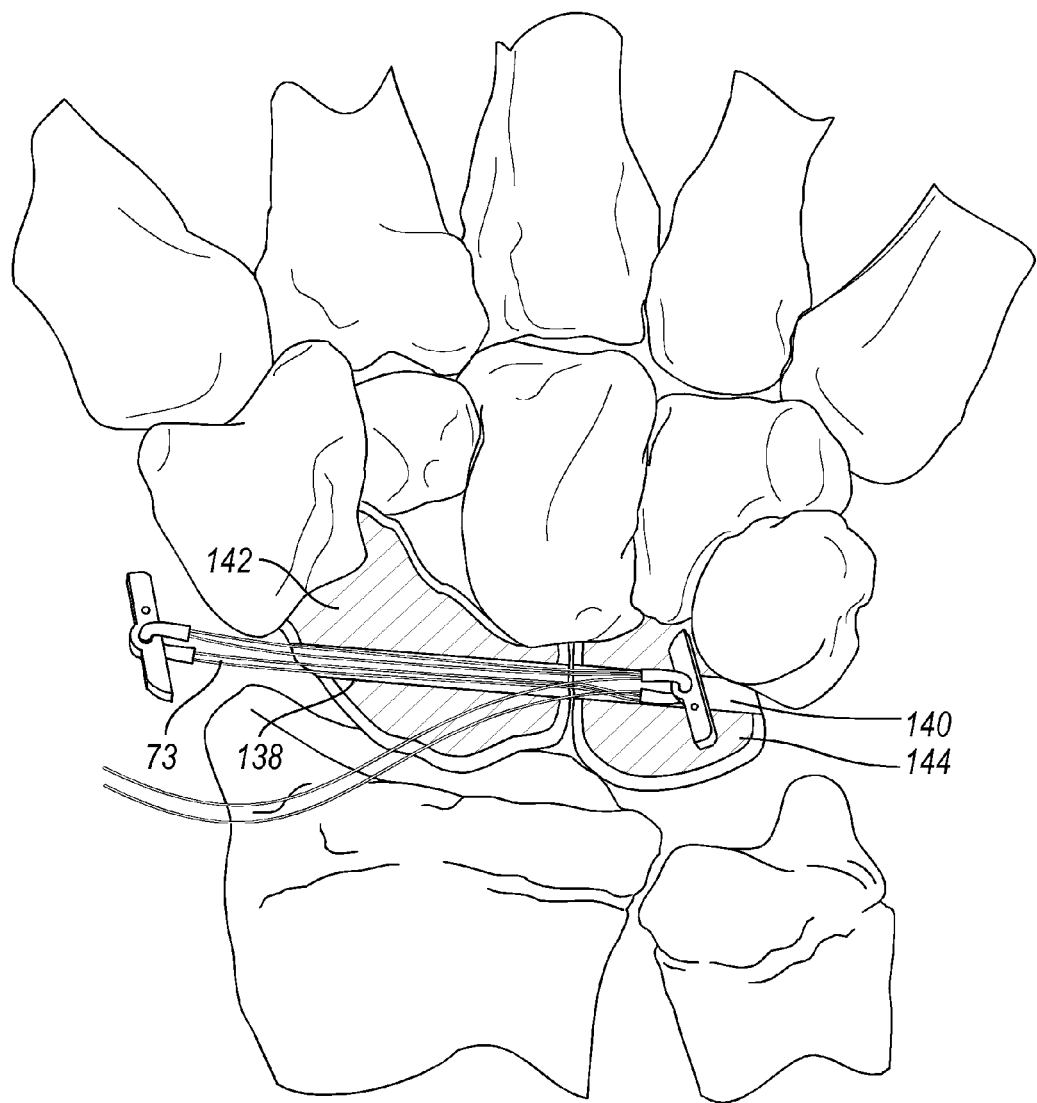
Figure 28:
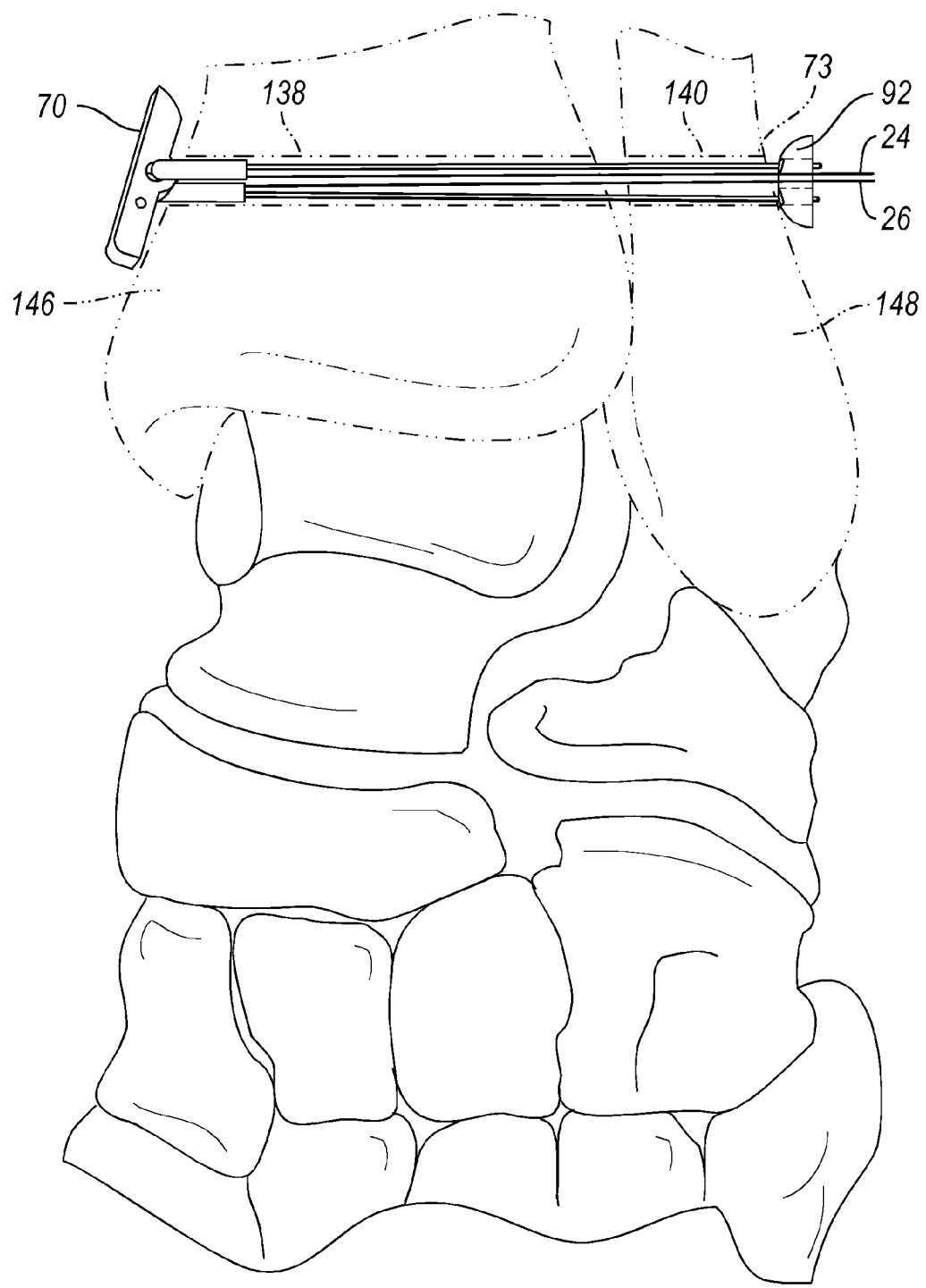

As shown in FIGS. 26-28, the suture construction 73 as shown in FIGS. 1-7 can be used to couple and position bony elements of a patient. FIG. 26 shows the coupling of a coracoid process 137 to the spine of scapula 139. In this regard, a pair of coaxial bores 138 and 140 are formed within the coracoid process 137 and spine of scapula 139. A pair of anchors 70, such as those shown in FIGS. 14-18, are coupled to a suture construction 73 such as the one shown in FIG. 2A or 4A. A first fastener 70 is fed through the aperture formed in the spine of scapula while the second fastener 70' is fed through the bore 140 formed in the coracoid process 137. Tension is applied to the ends 24 and 26 of the suture construction 73, pulling the bony structures into proper position.

The suture construction of FIGS. 1-7 allow for the alignment compression and/or positioning of the bone elements without the need to form knots.

Similarly, as shown in FIG. 27, the lunate 142 and scaphoid 144 can be drawn together using the construction 73 shown in FIG. 26. In this regard, it is envisioned that both the lunate 142 and scaphoid 144 can have appropriate bores 138 and 140 formed therein. These bores accept the suture construction 73 as shown in 26 to allow stabilization of the patient's anatomy.

As shown in FIG. 28, the radius 146 and ulna 148 can be coupled together by the use of a pair of axial suture accepting passages 138 and 140. In this configuration, the suture construction uses a first fastener 70 which is configured to pass through the passages 138 and 140. Additionally, the fastener 92 shown in FIG. 18 can be used as a load bearing member and bear against the ulna 148 and the application of tension to the ends 24 and 26 of the suture construction 73 tightens the suture construction and stabilizes the bones of the joint.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Such variations are not to be regarded as a departure from the spirit and scope of the invention.

What is claimed is:

1. A method of coupling a first portion of an anatomy to a second portion of the anatomy comprising:
   forming a first bore in a first bone of the anatomy;
   forming a second bore in a second bone of the anatomy;
   positioning a first anchor relative to the first bore;
   positioning a second anchor relative to the second bore, the second anchor having first and second adjustable suture constructs extending from the second anchor, each of the first and second adjustable suture constructs defining corresponding body portions;
   positioning the first and second adjustable suture constructs between the first and second bones;
   coupling the first and second adjustable suture constructs with corresponding first and second ligament replacements;
   tensioning at least one end of the first adjustable suture construct to tension the first ligament replacement, wherein tensioning at least one end of the first adjustable suture construct includes adjusting a size of first and second adjustable loops slidably passing through a longitudinal interior bore defined in a passage portion of the body portion of the first adjustable suture construct; and
   tensioning at least one end of the second adjustable suture construct to tension the second ligament replacement, wherein tensioning at least one end of the second adjustable suture construct includes adjusting a size of first and second adjustable loops slidably passing through a longitudinal interior bore defined in a passage portion of the body portion of the second adjustable suture construct.

2. The method of claim 1, wherein the first adjustable suture construct passes through a first through bore of the second anchor and wherein the second adjustable suture construct passes through a second through bore of the second anchor.

3. The method of claim 2, wherein the first and second adjustable loops of the first adjustable suture construct are coupled to a portion of the first ligament replacement positioned in the second bore of the second bone, and wherein the first and second adjustable loops of the second adjustable suture construct are coupled to a portion of the second ligament replacement positioned in the second bore of the second bone.

4. The method of claim 3, wherein the first anchor is coupled to portions of the first and second ligament replacement in the first bore of the first bone.

5. The method of claim 3, wherein first and second adjustable loops of the first adjustable suture construct are coupled to the first ligament replacement with a first fastener formed by a suture loop.

6. The method of claim 3, wherein first and second adjustable loops of the second adjustable suture construct are coupled to the second ligament replacement with a second fastener.

7. The method of claim 1, wherein the second anchor is a toggle anchor.

8. The method of claim 7, further comprising:
   passing the toggle anchor through the first bore of the first bone and through and outside the second bore of the second bone in a first orientation aligned with the corresponding first and second bores; and
   rotating the toggle anchor to a second orientation transverse to the first orientation outside the second bore of the second bone.

9. The method of claim 1, wherein the first adjustable suture construct has first and second ends, and the first end passes through a first aperture defined by the body portion and into the longitudinal internal bore of the passage portion and out a second aperture defined by the body portion to form the first adjustable loop of the first adjustable suture construct, and wherein the second end of the suture passes through a third aperture defined by the body portion and into the longitudinal internal bore and out a fourth aperture defined by the body portion to form the second adjustable loop of the first adjustable suture construct.

10. The method of claim 9, wherein the first aperture coincides with the fourth aperture and the second aperture coincides with the third aperture.

11. The method of claim 9, wherein the second adjustable suture construct has first and second ends, and the first end passes through a first aperture defined by the body portion and into the longitudinal internal bore of the passage portion and out a second aperture defined by the body portion to form the first adjustable loop of the second adjustable suture construct, and wherein the second end of the suture passes through a third aperture defined by the body portion and into the longitudinal internal bore and out a fourth aperture defined by the body portion to form the second adjustable loop of the second adjustable suture construct.

12. The method of claim 11, wherein the first aperture coincides with the fourth aperture and the second aperture coincides with the third aperture.

13. A method of coupling a first portion of an anatomy to a second portion of the anatomy comprising:
   forming a first bore in a first bone of the anatomy;
   forming a second bore in a second bone of the anatomy;
   positioning a first anchor relative to the first bore;
   positioning a second anchor relative to the second bore, wherein the second anchor has a first adjustable suture construct defining a body portion passing through a first transverse bore of the second anchor, and a second adjustable suture construct defining a body portion passing through a second transverse bore of the second anchor;

positioning the first and second adjustable suture constructs between the first and second bones;

coupling first and second adjustable suture loops of the first adjustable suture construct with a first ligament replacement, wherein the first and second adjustable suture loops slidably pass through a longitudinal interior bore defined in a passage portion of the body portion of the first adjustable suture construct;

coupling first and second adjustable suture loops of the second adjustable suture construct with a second ligament replacement, wherein the first and second adjustable suture loops slidably pass through a longitudinal interior bore defined in a passage portion of the body portion of the second adjustable suture construct;

tensioning at least one end of first and second ends of the first adjustable suture construct to adjust a size of the first and second adjustable loops and tension the first replacement ligament; and tensioning at least one end of first and second ends of the second adjustable suture construct to adjust a size of the first and second adjustable loops and tension the second ligament replacement.

14. The method of claim 13, wherein the first end of the first adjustable suture construct passes through a first aperture defined by the body portion and into the longitudinal internal bore of the passage portion and out a second aperture defined by the body portion to form the first adjustable loop of the first adjustable suture construct, and wherein the second end of the of the first adjustable suture construct passes through a third aperture defined by the body portion and into the longitudinal internal bore and out a fourth aperture defined by the body portion to form the second adjustable loop of the first adjustable suture construct.

15. The method of claim 14, wherein the first and second adjustable loops of the first adjustable suture construct extend outside the first and second bores, and wherein the first ligament replacement passes through the first and second adjustable loops of the first adjustable suture construct outside the first and second bores, and wherein the first and second adjustable loops of the second adjustable suture construct extend outside the first and second bores, and wherein the second replacement ligament passes through the first and second adjustable loops of the second adjustable suture construct outside the first and second bores.

16. A method of coupling a first portion of an anatomy to a second portion of the anatomy comprising:

forming a first bore in a first bone of the anatomy;

forming a second bore in a second bone of the anatomy;

positioning a first anchor relative to the first bore;

positioning a second anchor relative to the second bore, the second anchor having a first adjustable suture construct passing through a first transverse bore of the second anchor and extending from the second anchor and a second adjustable suture construct passing through a second transverse bore of the second anchor and extending from the second anchor, each of the first and second adjustable suture constructs defining corresponding body portions;

positioning the first and second adjustable suture constructs between the first and second anchors;

tensioning at least one end of the first adjustable suture construct, wherein tensioning at least one end of the first adjustable suture construct includes adjusting a size of first and second adjustable loops slidably passing through a longitudinal passage portion defined in the body portion of the first adjustable suture construct; and tensioning at least one end of the second adjustable suture construct, wherein tensioning at least one end of the second adjustable suture construct includes adjusting a size of first and second adjustable loops slidably passing through a longitudinal passage portion defined in the body portion of the second adjustable suture construct.

17. The method of claim 16, wherein the first end of the first adjustable suture construct passes through a first aperture defined by the body portion and into the longitudinal passage portion and out a second aperture defined by the body portion to form the first adjustable loop of the first adjustable suture construct, and wherein the second end of the of the first adjustable suture construct passes through a third aperture defined by the body portion and into the longitudinal passage portion and out a fourth aperture defined by the body portion to form the second adjustable loop of the first adjustable suture construct.

18. The method of claim 16, further comprising coupling the first and second adjustable suture loops of the first adjustable suture construct with a first ligament replacement and coupling first and second adjustable suture loops of the second adjustable suture construct with a second ligament replacement.

19. The method of claim 18, wherein tensioning at least one end of first and second ends of the first adjustable suture construct tensions the first replacement ligament and tensioning at least one end of first and second ends of the second adjustable suture construct tensions the second ligament replacement.

20. The method of claim 19, wherein the first and second adjustable loops of the first adjustable suture construct extend outside the first and second bores, and wherein the first ligament replacement passes through the first and second adjustable loops of the first adjustable suture construct outside the first and second bores, and wherein the first and second adjustable loops of the second adjustable suture construct extend outside the first and second bores, and wherein the second replacement ligament passes through the first and second adjustable loops of the second adjustable suture construct outside the first and second bores.

* * * * *

UNITED STATES PATENT AND TRADEMARK OFFICE
CERTIFICATE OF CORRECTION

PATENT NO. : 8,721,684 B2
APPLICATION NO. : 13/412127
DATED : May 13, 2014
INVENTOR(S) : Gregory J. Denham Page 1 of 1

It is certified that error appears in the above-identified patent and that said Letters Patent is hereby corrected as shown below:

In The Specification

Column 5, Line 10; Delete "tissue fastening members" and insert --bone engaging members--.

Column 5, Line 38; Delete "24, 26" and insert --46--.

Column 5, Line 64; Delete "20" and insert --22--.

Column 6, Line 63; Delete "26" and insert --24--.

Column 7, Line 57; Delete "64." and insert -64'.--.

In the Claims

Column 9, Line 64, In Claim 2; after "first", delete "through".

Column 9, Line 66, In Claim 2; after "second", delete "through".

Column 12, Line 26, In Claim 17; after "end", delete "of the".

Signed and Sealed this
Twenty-seventh Day of January, 2015

Michelle K. Lee
*Deputy Director of the United States Patent and Trademark Office*